(12) United States Patent
Shallom

(10) Patent No.: US 11,417,342 B2
(45) Date of Patent: Aug. 16, 2022

(54) SYNTHESIZING PATIENT-SPECIFIC SPEECH MODELS

(71) Applicant: Cordio Medical Ltd., Or Yehuda (IL)

(72) Inventor: Ilan D. Shallom, Gedera (IL)

(73) Assignee: CORDIO MEDICAL LTD., Or Yehuda (IL)

( * ) Notice: Subject to any disclaimer, the term of this patent is extended or adjusted under 35 U.S.C. 154(b) by 123 days.

(21) Appl. No.: 16/914,524

(22) Filed: Jun. 29, 2020

(65) Prior Publication Data

US 2021/0407519 A1  Dec. 30, 2021

(51) Int. Cl.
| | |
|---|---|
| A61B 5/00 | (2006.01) |
| G10L 17/14 | (2013.01) |
| G10L 17/16 | (2013.01) |
| G06N 3/06 | (2006.01) |
| G06N 3/04 | (2006.01) |
| G10L 15/16 | (2006.01) |
| G10L 15/07 | (2013.01) |
| G10L 15/065 | (2013.01) |

(52) U.S. Cl.
CPC .............. *G10L 17/14* (2013.01); *G06N 3/049* (2013.01); *G06N 3/06* (2013.01); *G10L 15/16* (2013.01); *G10L 17/16* (2013.01); *A61B 5/4803* (2013.01); *G10L 15/065* (2013.01); *G10L 15/07* (2013.01)

(58) Field of Classification Search
CPC ....... G10L 15/07; G10L 15/16; G10L 15/065; A61B 5/4803
See application file for complete search history.

(56) References Cited

U.S. PATENT DOCUMENTS

| | | | |
|---|---|---|---|
| 4,838,275 | A | 6/1989 | Lee |
| 5,853,005 | A | 12/1998 | Scanlon |

(Continued)

FOREIGN PATENT DOCUMENTS

| | | |
|---|---|---|
| CN | 102125427 A | 7/2011 |
| CN | 102423262 A | 4/2012 |

(Continued)

OTHER PUBLICATIONS

Ramirez et al.,"Voice activity detection. Fundamentals and speech recognition system robustness", Robust Speech Recognition and Understanding, I-Tech, Vienna, Austria, pp. 1-24, Jun. 2007.

(Continued)

*Primary Examiner* — Feng-Tzer Tzeng
(74) *Attorney, Agent, or Firm* — Kligler & Associates Patent Attorneys Ltd

(57) ABSTRACT

An apparatus includes a communication interface and a processor. The processor is configured to receive, via the communication interface, a plurality of speech samples $\{u_m^0\}$, m=1 . . . M, which were uttered by a subject while in a first state with respect to a disease, and using $\{u_m^0\}$ and at least one reference discriminator, which is not specific to the subject, synthesize a subject-specific discriminator, which is specific to the subject and is configured to generate, in response to one or more test utterances uttered by the subject, an output indicating a likelihood that the subject is in a second state with respect to the disease. Other embodiments are also described.

55 Claims, 4 Drawing Sheets

(56) References Cited

U.S. PATENT DOCUMENTS

| | | | |
|---|---|---|---|
| 5,864,810 A * | 1/1999 | Digalakis | G10L 17/00 704/254 |
| 6,168,568 B1 | 1/2001 | Gavriely | |
| 6,241,683 B1 | 6/2001 | Macklem et al. | |
| 6,289,313 B1 | 9/2001 | Heinonen et al. | |
| 6,389,393 B1 | 5/2002 | Gong | |
| 6,396,416 B1 | 5/2002 | Kuusela et al. | |
| 6,527,729 B1 | 3/2003 | Turcott | |
| 6,600,949 B1 | 7/2003 | Turcott | |
| 7,092,874 B2 | 8/2006 | Clavbo | |
| 7,225,013 B2 | 5/2007 | Geva et al. | |
| 7,226,422 B2 | 6/2007 | Hatlestsad et al. | |
| 7,267,652 B2 | 9/2007 | Coyle et al. | |
| 7,283,962 B2 | 10/2007 | Meyerhoif et al. | |
| 7,363,226 B2 | 4/2008 | Shiomi et al. | |
| 7,398,213 B1 | 7/2008 | Levanon et al. | |
| 7,457,753 B2 | 11/2008 | Moran et al. | |
| 7,529,670 B1 | 5/2009 | Michaelis | |
| 7,762,264 B1 | 7/2010 | Raming et al. | |
| 8,591,430 B2 | 11/2013 | Amurthur et al. | |
| 8,684,900 B2 | 4/2014 | Tran | |
| 8,689,606 B2 | 4/2014 | Schellekens et al. | |
| 8,784,311 B2 | 7/2014 | Shrivastav et al. | |
| 9,070,357 B1 | 6/2015 | Kennedy et al. | |
| 9,138,167 B1 | 9/2015 | Leydon | |
| 9,153,231 B1 * | 10/2015 | Salvador | G10L 15/16 |
| 9,445,763 B2 | 9/2016 | Davis et al. | |
| 9,492,096 B2 | 11/2016 | Brockway et al. | |
| 9,579,056 B2 | 2/2017 | Rosenbek et al. | |
| 9,685,174 B2 | 6/2017 | Karam et al. | |
| 9,922,641 B1 | 3/2018 | Chun | |
| 10,796,205 B2 | 10/2020 | Shi et al. | |
| 2002/0059029 A1 | 5/2002 | Fodder et al. | |
| 2003/0115054 A1 | 6/2003 | Iso-Sipila et al. | |
| 2003/0220790 A1 | 11/2003 | Kepuska | |
| 2004/0097822 A1 | 5/2004 | Muz et al. | |
| 2006/0058697 A1 | 3/2006 | Mochizuki et al. | |
| 2006/0116878 A1 | 6/2006 | Nagamine | |
| 2006/0167385 A1 | 7/2006 | Guion | |
| 2006/0293609 A1 | 12/2006 | Stahmann et al. | |
| 2007/0005357 A1 | 1/2007 | Moran et al. | |
| 2007/0225975 A1 | 9/2007 | Imoto | |
| 2008/0013747 A1 | 1/2008 | Tran | |
| 2008/0275349 A1 | 11/2008 | Halperin et al. | |
| 2009/0036777 A1 | 2/2009 | Zhang et al. | |
| 2009/0043586 A1 | 2/2009 | MacAuslan | |
| 2009/0099848 A1 | 4/2009 | Lerner et al. | |
| 2009/0326937 A1 | 12/2009 | Chitsaz et al. | |
| 2010/0201807 A1 | 8/2010 | McPherson | |
| 2011/0021940 A1 | 1/2011 | Chu et al. | |
| 2011/0092779 A1 | 4/2011 | Chang et al. | |
| 2011/0125044 A1 | 5/2011 | Rhee | |
| 2011/0184250 A1 | 7/2011 | Schmidt et al. | |
| 2012/0041279 A1 | 2/2012 | Freeman et al. | |
| 2012/0116186 A1 | 5/2012 | Shrivastav et al. | |
| 2012/0220899 A1 * | 8/2012 | Oh | A61B 7/003 600/586 |
| 2012/0283598 A1 | 8/2012 | Horii et al. | |
| 2012/0265024 A1 | 10/2012 | Shrivastav et al. | |
| 2013/0018274 A1 | 1/2013 | O'Neill | |
| 2013/0158434 A1 | 6/2013 | Shen et al. | |
| 2014/0005564 A1 | 1/2014 | Ivanovic et al. | |
| 2014/0073993 A1 | 3/2014 | Poellabauer et al. | |
| 2014/0153794 A1 | 6/2014 | Varaklis et al. | |
| 2014/0249424 A1 | 9/2014 | Fan et al. | |
| 2014/0302472 A1 | 10/2014 | Fletcher | |
| 2014/0314212 A1 | 10/2014 | Bentley et al. | |
| 2015/0073306 A1 | 3/2015 | Abeyratne et al. | |
| 2015/0126888 A1 | 5/2015 | Patel et al. | |
| 2015/0127350 A1 | 5/2015 | Agiomyrgiannakis | |
| 2015/0216448 A1 | 8/2015 | Lotan et al. | |
| 2015/0265205 A1 | 9/2015 | Rosenbek et al. | |
| 2016/0015289 A1 | 1/2016 | Simon et al. | |
| 2016/0045161 A1 | 2/2016 | Alshaer et al. | |
| 2016/0081611 A1 | 3/2016 | Hampton et al. | |
| 2016/0095545 A1 | 4/2016 | Levanon | |
| 2016/0249842 A1 | 9/2016 | Ohana Lubelchick | |
| 2016/0302003 A1 | 10/2016 | Rahman et al. | |
| 2017/0069312 A1 | 3/2017 | Sundararajan et al. | |
| 2017/0084295 A1 | 3/2017 | Tsiartas et al. | |
| 2017/0280239 A1 | 9/2017 | Sekiya et al. | |
| 2017/0325779 A1 | 11/2017 | Spina et al. | |
| 2018/0108440 A1 | 4/2018 | Stevens et al. | |
| 2018/0125444 A1 | 5/2018 | Kahlman et al. | |
| 2018/0296092 A1 | 10/2018 | Hassan et al. | |
| 2019/0080803 A1 | 3/2019 | Lotan et al. | |
| 2019/0130910 A1 | 5/2019 | Kariya et al. | |
| 2019/0221317 A1 | 7/2019 | Kempanna et al. | |
| 2019/0311815 A1 | 10/2019 | Kim et al. | |
| 2020/0118583 A1 | 4/2020 | Shallom et al. | |
| 2020/0152226 A1 | 5/2020 | Anushiravani et al. | |
| 2020/0168230 A1 | 5/2020 | Roh et al. | |
| 2020/0294527 A1 | 9/2020 | Shallom et al. | |
| 2020/0294531 A1 | 9/2020 | Shallom et al. | |

FOREIGN PATENT DOCUMENTS

| | | |
|---|---|---|
| CN | 202261466 U | 5/2012 |
| CN | 102497472 A | 6/2012 |
| CN | 107622797 A | 1/2018 |
| DE | 102015218948 A1 | 3/2017 |
| EP | 1855594 A1 | 11/2007 |
| EP | 2124223 A1 | 11/2009 |
| EP | 2438863 A1 | 4/2012 |
| GB | 1219618 A | 1/1971 |
| GB | 2493458 A | 2/2013 |
| JP | 04082538 A | 3/1992 |
| JP | 09173320 A | 7/1997 |
| SE | 508439 C2 | 10/1998 |
| WO | 2006079062 A1 | 7/2006 |
| WO | 2010015865 A1 | 2/2010 |
| WO | 2010123483 A2 | 10/2010 |
| WO | 2012038903 A2 | 3/2012 |
| WO | 2012104743 A2 | 8/2012 |
| WO | 2013043847 A1 | 3/2013 |
| WO | 2013170131 A1 | 11/2013 |
| WO | 2014037843 A1 | 3/2014 |
| WO | 2014045257 A1 | 3/2014 |
| WO | 2014188408 A1 | 11/2014 |
| WO | 2016028495 A1 | 2/2016 |
| WO | 2017060828 A1 | 4/2017 |
| WO | 2017068582 A1 | 7/2017 |
| WO | 2018021920 A1 | 2/2018 |
| WO | 2019210261 A1 | 10/2019 |

OTHER PUBLICATIONS

Bachu et al., "Separation of Voiced and Unvoiced Speech Signals using Energy and Zero Crossing Rate", ASEE Regional Conference, pp. 1-7, year 2008.

International Application # PCT/IB2020/054952 Search Report dated Sep. 19, 2021.

AU Application # 2019356224 Office Action dated Oct. 21, 2021.

EP Application # 20158069.3 Office Action dated Nov. 17, 2021.

Wikipedia, "Breathing," pp. 1-13, last edited Oct. 17, 2021, as downloaded from https://en.wikipedia.org/wiki/Breathing.

"Sound Speed in Gases," Sound and Hearing, HyperPhysics, Department of Physics and Astronomy, Georgia State University, USA, pp. 1-3, year 2017, as downloaded from http://hyperphysics.phy-astr.gsu.edu/hbase/Sound/souspe3.html.

"Echo Devices," Amazon.com, Inc, Interest-Based Ads, pp. 1-6, year 2021, as downloaded from https://www.amazon.com/echo-devices/s?k=echo+devices.

"The Best Google Home Speakers in 2021," Tom's Guide, Future US Inc., pp. 1-21, year 2021, as downloaded from https://www.tomsguide.com/best-picks/best-google-home-speakers.

West et al., "Measurements of Pulmonary Gas Exchange Efficiency using Expired Gas and Oximetry: Results in Normal Subjects," American Journal of Physiology—Lung Cellular and Molecular Physiology, vol. 314, No. 4, pp. L686-L689, year 2018.

(56) References Cited

OTHER PUBLICATIONS

West et al., "A New Method for Noninvasive Measurement of Pulmonary Gas Exchange Using Expired Gas," Respiratory Physiology & Neurobiology, vol. 247, pp. 112-115, year 2018.
Huang et al., "An Accurate Air Temperature Measurement System Based on an Envelope Pulsed Ultrasonic Time-of-Flight Technique," Review of Scientific Instruments, vol. 78, pp. 115102-1-115102-9, year 2007.
Jedrusyna, "An Ultrasonic Air Temperature Meter", Book "Recent Advances in Mechatronics", Springer, Berlin, Heidelberg, pp. 85-89, year 2010.
Cramer, "The Variation of the Specific Heat Ratio and the Speed of Sound in Air with Temperature, Pressure, Humidity, and $CO_2$ Concentration," Journal of the Acoustical Society of America, vol. 93, No. 5, pp. 2510-2516, May 1993.
Larson et al., "SpiroSmart: using a microphone to measure lung function on a mobile phone", Proceedings of the 2012 ACM Conference on Ubiquitous Computing (UbiComp '12), pp. 280-289, Sep. 5-8, 2012.
Abushakra et al., "An Automated Approach Towards Estimating Lung Capacity from Respiration Sounds", IEEE Healthcare Innovations Conference (HIC'12), pp. 1-5, Jan. 2012.
Williammson et al., "Vocal and Facial Biomarkers of Depression Based on Motor Incoordination and Timing", 4th International Audio/Visual Emotion Challenge and Workshop: Depression Challenge, Orlando, Florida, USA, pp. 1-8, Nov. 7, 2014.
Ciccarelli et al., "Neurophysiological Vocal Source Modeling for Biomarkers of Disease", Interspeech 2016: Understanding Speech Processing in Humans and Machines, Technical Program, San Francisco, USA, pp. 1-7, Sep. 8-12, 2016.
Helfer et al., "Classification of depression state based on articulatory precision", Proceedings of the 14th Annual Conference of the International Speech Communication Association (Interspeech), pp. 2172-2176, year 2013.
Horwitz., "Vocal Modulation Features in the Prediction of Major Depressive Disorder Severity", pp. 1-115, Master Thesis, Massachusetts Institute of Technology, Sep. 2014.
Hillel., "Using phonation time to estimate vital capacity in amyotrophic lateral sclerosis", Arch Phys Med Rehabil, vol. 70, pp. 618-620, Aug. 1989.
Yanagihara., "Phonation and Respiration", Folia Phoniat, vol. 18, pp. 323-340, 1966.
Dewar et al., "Chronic obstructive pulmonary disease: diagnostic considerations", American Academy of Family Physicians, vol. 73, pp. 669-676, Feb. 2006.
Solomon et al., "Respiratory and laryngeal contributions to maximum phonation duration", Journal of voice, vol. 14, No. 3, pp. 331-340, Sep. 2000.
Dogan et al., "Subjective and objective evaluation of voice quality in patients with asthma", Journal of voice, vol. 21, No. 2, pp. 224-230, Mar. 2007.
Orenstein et al.,"Measuring ease of breathing in young patients with cystic fibrosis", Pediatric Pulmonology, vol. 34, No. 6, pp. 473-477, Aug. 8, 2002.
Lee et al., "Speech Segment Durations Produced by Healthy and Asthmatic Subjects", Journal of Speech and Hearing Disorders, vol. 653, pp. 186-193, May 31, 1988.
Hickey, "App lets you monitor lung health using only a smartphone", pp. 1-5, Sep. 18, 2012.
Gandler et al., "Mobile FEV: Evaluation of iPhone Spirometer", 1 page, Feb. 14, 2013.
Abushakra et al., "Lung capacity estimation through acoustic signal of breath", 13th IEEE International Conference an BioInformatics and BioEngineering, pp. 386-391, Nov. 11-13, 2012.
G.P. Imports, Inc., "Spirometer Pro", pp. 1-3, Jan. 8, 2010.
Murton et al., "Acoustic speech analysis of patients with decompensated heart failure: A pilot study", The Journal of the Acoustical Society of America, vol. 142, Issue 4, pp. 1-28, Oct. 24, 2017.
Gillespie et al., "The Effects of Hyper- and Hypocapnia on Phonatory Laryngeal Airway Resistance in Women", Research Article, Journal of Speech, Language, and 638 Hearing Research , vol. 58 , pp. 638-652, Jun. 2015.
Wang et al., "Accuracy of perceptual and acoustic methods for the detection of inspiratory loci in spontaneous speech", Behavior Research Methods, vol. 44, Issue 4, pp. 1121-1128, Dec. 2012.
Mulligan et al., "Detecting regional lung properties using audio transfer functions of the respiratory system", 31st Annual International Conference of the IEEE EMBS, pp. 5697-5700, Sep. 2-6, 2009.
Walia et al., "Level of Asthma: A Numerical Approach based on Voice Profiling", IJEDR(International Journal of Engineering Development and Research),vol. 4, Issue 4, pp. 717-722, 2016.
Sakoe et al., "Dynamic Programming Algorithm Optimization for Spoken Word Recognition", IEEE Transactions on Acoustics, Speech and Signal Processing, vol. ASSP-26, No. 1, pp. 43-49, Feb. 1978.
Rabiner, L., "A tutorial on hidden Markov models and selected applications in speech recognition," Proceedings of the IEEE, vol. 77, issue 2 , pp. 257-286, Feb. 1989.
Rabiner et al., "Fundamentals of Speech Recognition", Prentice Hall, pp. 1-18 (related section 6.4.3.), year 1993.
Lee et al., Consistency of acoustic and aerodynamic measures of voice production over 28 days under various testing conditions, Journal of Voice, Elsevier Science , US, vol. 13, Issue 4, pp. 477-483, Dec. 1, 1999.
Shallom et al., U.S. Appl. No. 16/807,178, filed Mar. 3, 2020.
Ney, "The Use of a One-Stage Dynamic Programming Algorithm for Connected Word Recognition," IEEE Transactions on Acoustics, Speech, and Signal Processing, vol. ASSP-32, No. 2, pp. 263-271, Apr. 1984.
U.S. Appl. No. 16/157,118 office action dated May 5, 2020.
International Application # PCT/IB2020/051016 search report dated May 21, 2020.
International Application # PCT/IB2020/051018 search report dated Jun. 2, 2020.
European Application # 20158058.6 search report dated Jul. 23, 2020.
European Application # 20158069.3 search report dated Jul. 24, 2020.
Japanese Application # 2018-516182 office action action dated Jul. 15, 2020.
Christina et al., "HMM-based speech recognition system for the dysarthric speech evaluation of articulatory subsystem", International Conference on Recent Trends in Information Technology, pp. 54-59, Apr. 1, 2012.
Wang et al., "Vocal folds disorder detection using pattern recognition methods", 29th Annual International Conference of the IEEE Engineering in Medicine and Biology Society, pp. 3253-3256, Aug. 22-26, 2007.
Rabiner., "A Tutorial on Hidden Markov Models and Selected Applications in Speech Recognition", Proceedings of the IEEE, vol. 77, issue 2, pp. 257-286, Feb. 1989.
Masada et al., "Feature Extraction by ICA and Clustering for Lung Sound Classification", IPSJ Symposium Series, vol. 2007, pp. 1-9, year 2007.
Rao et al., "Acoustic Methods for Pulmonary Diagnosis," HHS Public Access, Author manuscript, pp. 1-39, year 2020 (final version published in IEEE Reviews in Biomedical Engineering, vol. 12, pp. 221-239, year 2019).
International Application # PCT/IB2021/051459 Search Report dated May 25, 2021.
EP Application # 21158827.2 Search Report dated Jul. 28, 2021.
Cohen, "Signal processing methods for upper airway and pulmonary dysfunction diagnosis," IEEE Engineering in Medicine and Biology Magazine, vol. 9, No. 1, pp. 72-75, Mar. 1, 1990.
AU Application # 2019356224 Office Action dated Jan. 17, 2022.
International Application # PCT/IB2021/054952 Search Report dated Jan. 30, 2022.
U.S. Appl. No. 16/807,178 Office Action dated Feb. 24, 2022.
Gupta et al., "Characterizing Exhaled Airflow from Breathing and Talking," Indoor Air, vol. 20, pp. 31-39, year 2010.
U.S. Appl. No. 17/074,653 Office Action dated Mar. 9, 2022.

(56) References Cited

OTHER PUBLICATIONS

Bhagya et al., "Speed of Sound-Based Capnographic Sensor with Second-Generation CNN for Automated Classification of Cardiorespiratory Abnormalities," IEEE Sensors Journal, vol. 19, issue 19, pp. 8887-8894, Oct. 1, 2019.
Mirza et al., "Analytical Modeling and Simulation of a CMOS-MEMS Cantilever Based CO2 Sensor for Medical Applications," Proceedings IEEE Regional Symposium on Micro and Nanoelectronics, pp. 70-73, Sep. 27, 2013.
International Application # PCT/IB2021/060800 Search Report dated Mar. 21, 2022.
IN Application # 202147045402 Office Action dated Mar. 14, 2022.
EP Application # 21209891.7 Search Report dated Apr. 13, 2022.
IN Application # 202147045344 Office Action dated Apr. 1, 2022.

* cited by examiner

SYNTHESIZING PATIENT-SPECIFIC SPEECH MODELS

FIELD OF THE INVENTION

The present invention is related to the field of speech-signal processing, particularly for diagnostic purposes.

BACKGROUND

Sakoe and Chiba, "Dynamic Programming Algorithm Optimization for Spoken Word Recognition," IEEE Transactions on Acoustics, Speech, and Signal Processing 26.2 (1978): 43-49, which is incorporated herein by reference, reports on an optimum dynamic programming (DP) based time-normalization algorithm for spoken word recognition. First, a general principle of time-normalization is given using a time-warping function. Then, two time-normalized distance definitions, called symmetric and asymmetric forms, are derived from the principle. These two forms are compared with each other through theoretical discussions and experimental studies. The symmetric form algorithm superiority is established. A technique, called slope constraint, is introduced, in which the warping function slope is restricted so as to improve discrimination between words in different categories.

Rabiner, Lawrence R., "A tutorial on hidden Markov models and selected applications in speech recognition," Proceedings of the IEEE 77.2 (1989): 257-286, which is incorporated herein by reference, reviews theoretical aspects of types of statistical modeling, and shows how they have been applied to selected problems in machine recognition of speech.

U.S. Pat. No. 5,864,810 describes a method and apparatus for automatic recognition of speech, which adapts to a particular speaker by using adaptation data to develop a transformation through which speaker independent models are transformed into speaker adapted models. The speaker adapted models are then used for speaker recognition and achieve better recognition accuracy than non-adapted models. In a further embodiment, the transformation-based adaptation technique is combined with a known Bayesian adaptation technique.

U.S. Pat. No. 9,922,641 describes a method that includes receiving input speech data from a speaker in a first language, and estimating, based on a universal speech model, a speaker transform representing speaker characteristics associated with the input speech data. The method also includes accessing a speaker-independent speech model for generating speech data in a second language that is different from the first language. The method further includes modifying the speaker-independent speech model using the speaker transform to obtain a speaker-specific speech model, and generating speech data in the second language using the speaker-specific speech model.

SUMMARY OF THE INVENTION

There is provided, in accordance with some embodiments of the present invention, an apparatus including a communication interface and a processor. The processor is configured to receive, via the communication interface, a plurality of speech samples $\{u_m^0\}$, m=1 ... M, which were uttered by a subject while in a first state with respect to a disease, and using $\{u_m^0\}$ and at least one reference discriminator, which is not specific to the subject, synthesize a subject-specific discriminator, which is specific to the subject and is configured to generate, in response to one or more test utterances uttered by the subject, an output indicating a likelihood that the subject is in a second state with respect to the disease.

In some embodiments, the first state is a stable state and the second state is an unstable state.

In some embodiments, the disease is selected from the group of diseases consisting of: congestive heart failure (CHF), coronary heart disease, arrhythmia, chronic obstructive pulmonary disease (COPD), asthma, interstitial lung disease, pulmonary edema, pleural effusion, Parkinson's disease, and depression.

In some embodiments, the processor is configured to synthesize the subject-specific discriminator by:

generating a first-state subject-specific speech model $\theta^0$ that returns, for any speech sample s, a first distance measure indicative of a first degree of similarity between s and first-state speech of the subject, and generating a second-state subject-specific speech model $\theta^1$ that returns a second distance measure indicative of a second degree of similarity between s and second-state speech of the subject.

In some embodiments, the at least one reference discriminator includes K reference discriminators $\{\varphi_k\}$, k=1 ... K, $\{\varphi_k\}$ including:

respective first-state reference speech models that return respective first distances $\{D_k^0(s)\}$, which indicate first degrees of similarity between s and respective reference first-state speech uttered by K groups of one or more other subjects, and respective second-state reference speech models that return respective second distances $\{D_k^1(s)\}$, which indicate second degrees of similarity between s and respective reference second-state speech uttered by the groups, $\theta^0$ returning the first distance measure by applying a function to $\{D_k^0(s)\}$, and $\theta^1$ returning the second distance measure by applying the function to $\{D_k^1(s)\}$.

In some embodiments, the function, when applied to $\{D_k^0(s)\}$, returns a weighted average of $\{D'^0_k(s)\}$, $D'^0_k(s)$ being a non-decreasing function of $D_k^0(s)$.

In some embodiments, the weighted average is $\Sigma_{k=1}^K w_k D'^0_k(s)$ for K weights $\{w_k\}$, k=1 ... K, that minimize a sum of respective distance measures for $\{u_m^0\}$ with respect to a constraint, the distance measure for each speech sample $u_m$ belonging to $\{u_m^0\}$ being based on $\Sigma_{k=1}^K w_k D'^0_k(u_m)$.

In some embodiments, the at least one reference discriminator includes:

a first-state reference speech model that returns a first distance $D^0(s)$, which indicates a first degree of similarity between s and reference first-state speech, and a second-state reference speech model that returns a second distance $D^1(s)$, which indicates a second degree of similarity between s and reference second-state speech.

In some embodiments, the first-state reference speech model returns $D^0(s)$ by applying a first function to a set of feature vectors $V(s)$ extracted from s, the second-state reference speech model returns $D^1(s)$ by applying a second function to $V(s)$, and generating $\theta^0$ and $\theta^1$ includes generating $\theta^0$ and $\theta^1$ using a normalizing transformation T that optimally transforms $\{V(u_m^0)\}$ under one or more predefined constraints.

In some embodiments, T minimizes $\Sigma_{u \in \{u_m^0\}} \Delta(T(V(u)), V(u_0))$ with respect to a constraint, $\Delta$ being a third distance measure between any two sets of features, and $u_0$ being a canonical utterance of content of $u \in \{u_m^0\}$.

In some embodiments, $\Delta$ is a non-decreasing function of a Dynamic Time Warping (DTW) distance.

In some embodiments, T minimizes $\Sigma_{u \in \{u_m^0\}} f'_0 T(V(u)))$ with respect to a constraint, $f_0$ being a non-decreasing function of the first function.

In some embodiments,
$\theta^0$ returns the first distance measure by applying the first function to $T(V(s))$, and
$\theta^1$ returns the second distance measure by applying the second function to $T(V(s))$.

In some embodiments,
generating $\theta^0$ includes generating $\theta^0$ by applying a denormalizing transformation T', which optimally transforms first parameters of the first-state reference speech model under one or more predefined constraints, to the first parameters, and
generating $\theta^1$ includes generating $\theta^1$ by applying T' to second parameters of the second-state reference speech model.

In some embodiments, T' minimizes $\Sigma_{u \in \{u_m^0\}} T'(D^0)(u)$ under the constraints, $T'(D^0)(s)$ being the first distance returned by the first-state reference speech model under the transformation.

In some embodiments,
the first-state reference speech model includes a first Hidden Markov Model (HMM) including multiple first kernels, the first parameters including first-kernel parameters of the first kernels, and
the second-state reference speech model includes a second HMM including multiple second kernels, the second parameters including second-kernel parameters of the second kernels.

In some embodiments, the first kernels and second kernels are Gaussian, and T' includes:
an affine transformation operating on a mean vector of any one or more Gaussian kernels, and
a quadratic transformation operating on a covariance matrix of any one or more Gaussian kernels.

In some embodiments,
the first-state reference speech model includes multiple first reference frames, the first parameters including first-reference-frame features of the first reference frames, and
the second-state reference speech model includes multiple second reference frames, the second parameters including second-reference-frame features of the second reference frames.

In some embodiments,
the reference first-state speech includes multiple first-state reference speech samples uttered by a first subset of R other subjects,
the reference second-state speech includes multiple second-state reference speech samples uttered by a second subset of the other subjects, and
the processor is further configured to:
identify respective transformations $\{T_r\}$, $r=1 \ldots R$, for the other subjects, $T_r$ being, for each $r^{th}$ one of the other subjects, a normalizing transformation that optimally transforms $\{\Phi_r\}$ under one or more predefined constraints, $\{\Phi_r\}$ being a union of (i) those of the first-state reference speech samples uttered by the other subject and (ii) those of the second-state reference speech samples uttered by the other subject,
compute modified sets of features by, for each $r^{th}$ one of the other subjects, applying $T_r$ to $\{V(\Phi_r)\}$, and
generate the reference discriminator from the modified sets of features.

In some embodiments,
the first-state reference speech model and the second-state reference speech model are identical with respect to a first set of parameters and differ from one another with respect to a second set of parameters,
the processor is configured to generate $\theta^0$ such that $\theta^0$ is identical to the first-state reference speech model with respect to the second set of parameters, and
the processor is configured to generate $\theta^1$ such that $\theta^1$ is identical to $\theta^0$ with respect to the first set of parameters and identical to the second-state reference speech model with respect to the second set of parameters.

In some embodiments,
the first-state reference speech model and the second-state reference speech model include different respective Hidden Markov Models (HMMs), each including multiple kernels having respective kernel weights,
the first set of parameters includes the kernel weights, and
the second set of parameters includes kernel-parameters of the kernels.

In some embodiments,
the at least one reference discriminator includes a reference neural network associated with multiple parameters, which returns, for any one or more speech samples, another output indicating a likelihood of the speech samples having been uttered in the second state, and
the processor is configured to synthesize the subject-specific discriminator by synthesizing a subject-specific neural network, by tuning a subset of the parameters so as to minimize an error of the other output for a set of input speech samples that includes $\{u_m^0\}$.

In some embodiments, the parameters include a plurality of neuronal weights, and the subset of the parameters includes a subset of the weights.

In some embodiments, the reference neural network includes multiple layers, and the subset of the weights includes at least some of the weights associated with one of the layers but does not include any of the weights associated with another one of the layers.

In some embodiments,
the layers include (i) one or more acoustic layers of neurons, which generate an acoustic-layer output in response to an input based on the speech samples, (ii) one or more phonetic layers of neurons, which generate a phonetic-layer output in response to the acoustic-layer output, and (iii) one or more discriminative layers of neurons, which generate the other output in response to the phonetic-layer output, and
the subset of the weights includes at least some of the weights associated with the acoustic layers and the discriminative layers but does not include any of the weights associated with the phonetic layers.

In some embodiments, the subset of the parameters includes a speaker-identifying parameter identifying a speaker of the speech samples.

In some embodiments, the set of input speech samples further includes one or more second-state speech samples.

There is further provided, in accordance with some embodiments of the present invention, a method including receiving a plurality of speech samples $\{u_m^0\}$, $m=1 \ldots M$, which were uttered by a subject while in a first state with respect to a disease. The method further includes, using $\{u_m^0\}$ and at least one reference discriminator, which is not specific to the subject, synthesizing a subject-specific discriminator, which is specific to the subject and is configured to generate, in response to one or more test utterances uttered by the subject, an output indicating a likelihood that the subject is in a second state with respect to the disease.

There is further provided, in accordance with some embodiments of the present invention, a computer software product including a tangible non-transitory computer-readable medium in which program instructions are stored. The instructions, when read by a processor, cause the processor to receive a plurality of speech samples $\{u_m^0\}$, m=1 ... M, which were uttered by a subject while in a first state with respect to a disease, and using $\{u_m^0\}$ and at least one reference discriminator, which is not specific to the subject, synthesize a subject-specific discriminator, which is specific to the subject and is configured to generate, in response to one or more test utterances uttered by the subject, an output indicating a likelihood that the subject is in a second state with respect to the disease.

The present invention will be more fully understood from the following detailed description of embodiments thereof, taken together with the drawings, in which:

DETAILED DESCRIPTION OF EMBODIMENTS

Glossary

Figure 1:
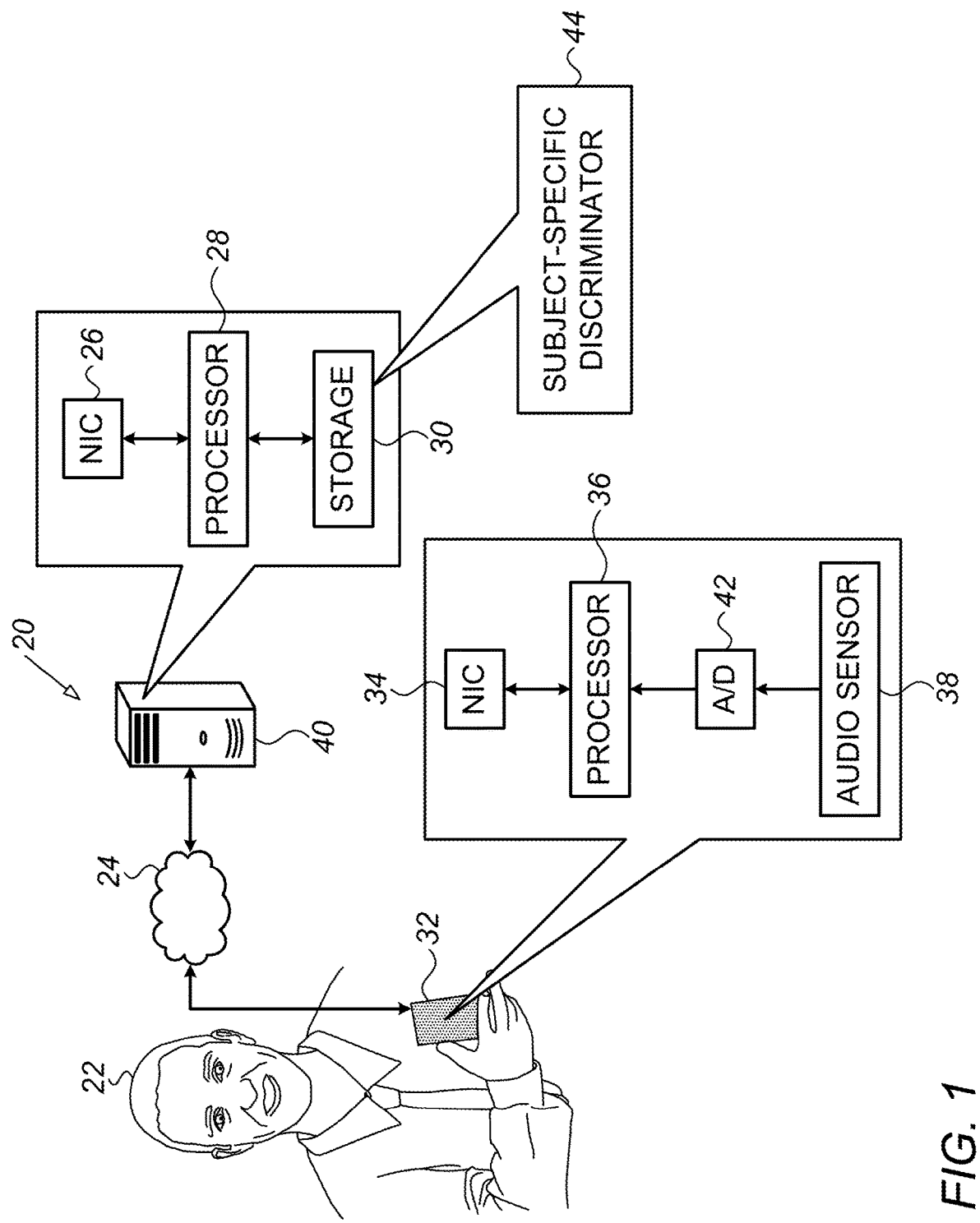
FIG. 1 is a schematic illustration of a system for evaluating the physiological state of a subject, in accordance with some embodiments of the present invention.

In the context of the present application, including the claims, a subject is said to be in an "unstable state" with respect to a physiological condition (or "disease") if the subject is suffering from an acute worsening of the condition. Otherwise, the subject is said to be in a "stable state" with respect to the condition.

In the context of the present application, including the claims, a "speech model" refers to a computer-implemented function configured to map a speech sample to an output indicating a property of the sample. For example, given a speech sample s uttered by a subject, a speech model may return a distance measure D(s) indicating a degree of similarity between s and reference speech of the subject or of other subjects.

In the context of the present application, including the claims, a "discriminator" refers to a group of one or more models, typically machine-learned models, configured to discriminate between various states. For example, given a set of states, such as "stable" and "unstable," with respect to a particular physiological condition, a discriminator may, based on a speech sample of a subject, generate an output indicating the likelihood that the subject is in one of the states.

Overview

For a subject who suffers from a physiological condition, it may be desired to train a discriminator configured to ascertain, based on the subject's speech, whether the subject is in a stable state or an unstable state with respect to the condition. A challenge, however, is that it may be difficult to acquire a sufficient number of training samples for each of the states. For example, for a subject who is generally stable, a sufficient number of speech samples uttered while in the stable state might be available, but it may be difficult to acquire a sufficient number of speech samples uttered while in the unstable state. For other subjects, it may be straightforward to collect a sufficient number of unstable-state samples (e.g., following admittance of the subject to a hospital), but not a sufficient number of stable-state samples.

To address this challenge, embodiments of the present invention generate a subject-specific discriminator, which is specific to the subject (i.e., is configured to discriminate for the subject), from a reference discriminator, which is not specific to the subject. To generate the subject-specific discriminator, the processor uses speech samples uttered by the subject while in one of the states to modify, or adapt, the reference discriminator. This process is referred to as a "synthesis" of the subject-specific discriminator, given that, advantageously, no speech samples uttered by the subject while in the other state are required.

The techniques described herein may be used to synthesize a discriminator for any suitable physiological condition such as congestive heart failure (CHF), coronary heart disease, atrial fibrillation or any other type of arrhythmia, chronic obstructive pulmonary disease (COPD), asthma, interstitial lung disease, pulmonary edema, pleural effusion, Parkinson's disease, or depression.

System Description

Reference is initially made to FIG. 1, which is a schematic illustration of a system 20 for evaluating the physiological state of a subject 22, in accordance with some embodiments of the present invention.

System 20 comprises an audio-receiving device 32, such as a mobile phone, a tablet computer, a laptop computer, a desktop computer, a voice-controlled personal assistant (such as an Amazon Echo™ or a Google Home™ device), a smart speaker device, or a dedicated medical device used by subject 22. Device 32 comprises circuitry including an audio sensor 38 (e.g., a microphone), which converts sound waves to analog electric signals, an analog-to-digital (A/D) converter 42, a processor 36, and a network interface, such as a network interface controller (NIC) 34. Typically, device 32 further comprises a storage device such as a solid-state drive, a screen (e.g., a touchscreen), and/or other user interface components, such as a keyboard and a speaker. In some embodiments, audio sensor 38 (and, optionally, A/D converter 42) belong to a unit that is external to device 32. For example, audio sensor 38 may belong to a headset that is connected to device 32 by a wired or wireless connection, such as a Bluetooth connection.

System 20 further comprises a server 40, comprising circuitry including a processor 28, a storage device 30, such as a hard drive or flash drive, and a network interface, such as a network interface controller (NIC) 26. Server 40 may further comprise a screen, a keyboard, and/or any other suitable user interface components. Typically, server 40 is located remotely from device 32, e.g., in a control center, and server 40 and device 32 communicate with one another, via their respective network interfaces, over a network 24, which may include a cellular network and/or the Internet.

System 20 is configured to evaluate the subject's physiological state by processing one or more speech signals (also referred to herein as "speech samples") received from the subject. Typically, processor 36 of device 32 and processor 28 of server 40 cooperatively perform the receiving and processing of at least some of the speech samples. For example, as the subject speaks into device 32, the sound waves of the subject's speech may be converted to an analog signal by audio sensor 38, which may in turn be sampled and digitized by A/D converter 42. (In general, the subject's speech may be sampled at any suitable rate, such as a rate of between 8 and 45 kHz.) The resulting digital speech signal may be received by processor 36. Processor 36 may then communicate the speech signal, via NIC 34, to server 40, such that processor 28 receives the speech signal via NIC 26. Subsequently, processor 28 may process the speech signal.

To process the subject's speech signals, processor 28 uses a subject-specific discriminator 44, which is specific to subject 22 and is stored in storage device 30. Based on each input speech signal, the subject-specific discriminator generates an output indicating a likelihood that the subject is in a particular physiological state. For example, the output may indicate a likelihood that the subject is in a stable state, and/or a likelihood that the subject is in an unstable state, with respect to a physiological condition. Alternatively or additionally, the output may include a score indicating the degree to which the subject's state appears to be unstable. Processor 28 is further configured to synthesize subject-specific discriminator 44 prior to using the subject-specific discriminator, as described in detail below with reference to the subsequent figures.

In response to the output from the subject-specific discriminator, the processor may generate any suitable audio or visual output to the subject and/or to another person, such as the subject's physician. For example, processor 28 may communicate the output to processor 36, and processor 36 may then communicate the output to the subject, e.g., by displaying a message on the screen of device 32. Alternatively or additionally, in response to the subject-specific discriminator outputting a relatively high likelihood that the subject's state is unstable, the processor may generate an alert indicating that the subject should take medication or visit a physician. Such an alert may be communicated by placing a call or sending a message (e.g., a text message) to the subject, to the subject's physician, and/or to a monitoring center. Alternatively or additionally, in response to the output from the discriminator, the processor may control a medication-administering device so as to adjust an amount of medication administered to the subject.

In other embodiments, subsequently to synthesizing the subject-specific discriminator, processor 28 communicates the subject-specific discriminator to processor 36, and processor 36 then stores the discriminator in a storage device belonging to device 32. Subsequently, processor 36 may use the discriminator to assess the physiological state of subject 22. As yet another alternative, even the synthesis of the subject-specific discriminator may be performed by processor 36. (Notwithstanding the above, the remainder of the present description, for simplicity, generally assumes that processor 28—also referred to hereinbelow simply as "the processor"—performs the synthesis.)

In some embodiments, device 32 comprises an analog telephone that does not comprise an A/D converter or a processor. In such embodiments, device 32 sends the analog audio signal from audio sensor 38 to server 40 over a telephone network. Typically, in the telephone network, the audio signal is digitized, communicated digitally, and then converted back to analog before reaching server 40. Accordingly, server 40 may comprise an A/D converter, which converts the incoming analog audio signal—received via a suitable telephone-network interface—to a digital speech signal. Processor 28 receives the digital speech signal from the A/D converter, and then processes the signal as described above. Alternatively, server 40 may receive the signal from the telephone network before the signal is converted back to analog, such that the server need not necessarily comprise an A/D converter.

As further described below with reference to the subsequent figures, processor 28 uses training speech samples, which were uttered by subject 22 while in a known physiological state, to synthesize subject-specific discriminator 44. Each of these samples may be received via a network interface, as described above, or via any other suitable communication interface, such as a flash-drive interface. Similarly, at least one reference discriminator that is not specific to subject 22, which is also used to synthesize the subject-specific discriminator, or training samples from other subjects that may be used to generate the reference discriminator, may be received by processor 28 via any suitable communication interface.

Processor 28 may be embodied as a single processor, or as a cooperatively networked or clustered set of processors. For example, a control center may include a plurality of interconnected servers comprising respective processors, which cooperatively perform the techniques described herein. In some embodiments, processor 28 belongs to a virtual machine.

In some embodiments, the functionality of processor 28 and/or of processor 36, as described herein, is implemented solely in hardware, e.g., using one or more Application-Specific Integrated Circuits (ASICs) or Field-Programmable Gate Arrays (FPGAs). In other embodiments, the functionality of processor 28 and of processor 36 is implemented at least partly in software. For example, in some embodiments, processor 28 and/or processor 36 is embodied as a programmed digital computing device comprising at least a central processing unit (CPU) and random access memory (RAM). Program code, including software programs, and/or data are loaded into the RAM for execution and processing by the CPU. The program code and/or data may be downloaded to the processor in electronic form, over a network, for example. Alternatively or additionally, the program code and/or data may be provided and/or stored on non-transitory tangible media, such as magnetic, optical, or electronic memory. Such program code and/or data, when provided to the processor, produce a machine or special-purpose computer, configured to perform the tasks described herein.

Synthesizing the Subject-Specific Discriminator

As described above in the Overview, conventional techniques for generating a discriminator for discriminating between two states typically requires a sufficient number of training samples for each of the states. However, in some situations, the processor may have sufficient training samples for only one of the states. To address such situations, the processor synthesizes the subject-specific discriminator.

To perform this synthesis, the processor first receives a plurality of speech samples $\{u_m^0\}$, m=1 ... M, which were uttered by the subject while in a first state (e.g., a stable state) with respect to a disease. Next, using $\{u_m^0\}$ and at least one reference discriminator, which is not specific to the subject, the processor synthesizes the subject-specific discriminator. Advantageously, despite the processor having few or no speech samples uttered by the subject while in the second state (e.g., an unstable state) with respect to the disease, the subject-specific discriminator may generate, in response to one or more test utterances uttered by the subject, an output indicating a likelihood that the subject is in the second state.

Multi-Model Discriminators

In some embodiments, the subject-specific discriminator includes a first-state subject-specific speech model $\theta^0$ and a second-state subject-specific speech model $\theta^1$. For any speech sample s, $\theta^0$ returns a first distance measure indicative of a degree of similarity between s and first-state speech of the subject, while $\theta^1$ returns a second distance measure indicative of a degree of similarity between s and second-state speech of the subject. In such embodiments, the subject-specific discriminator may generate an output based on a comparison of the two distance measures to one another. For example, assuming a convention in which a greater distance indicates less similarity, the subject-specific discriminator may generate an output indicating that the subject is likely in the first state in response to the ratio between the first distance measure and the second distance measure being less than a threshold. Alternatively, the subject-specific discriminator may output respective likelihoods for the two states based on the distance measures, or simply output the two distance measures.

To synthesize such a multi-model discriminator, various techniques may be used. Examples of such techniques are hereby described with reference to FIGS. 2-4.

(i) First Technique

Figure 2:
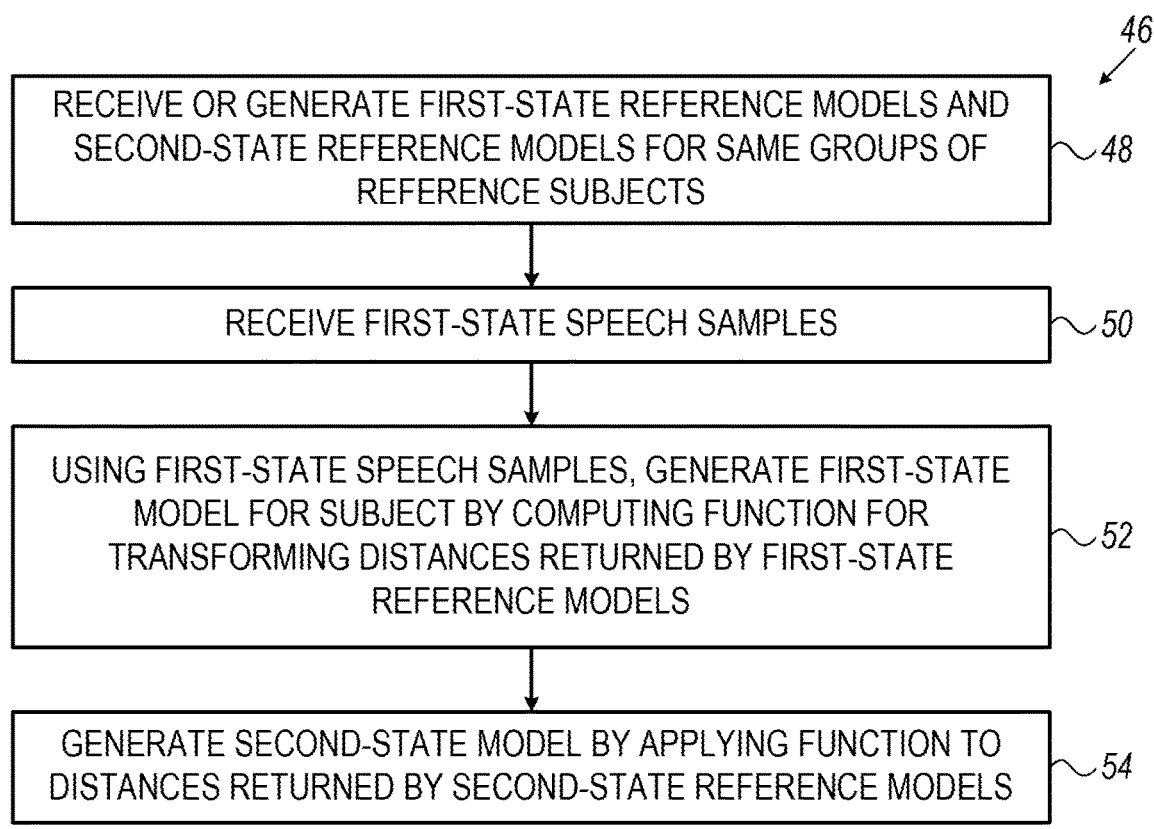
FIGS. 2-4 are flow diagrams for techniques for generating subject-specific speech models, in accordance with some embodiments of the present invention.

Reference is now made to FIG. 2, which is a flow diagram for a first technique 46 for generating $\theta^0$ and $\theta^1$, in accordance with some embodiments of the present invention.

Technique 46 begins at a first receiving-or-generating step 48, at which the processor receives or generates K≥1 reference discriminators $\{\varphi_k\}$, k=1 . . . K. (It is noted that the processor may receive some of the discriminators while generating others of the discriminators.) $\{\varphi_k\}$ comprise respective first-state reference speech models and respective second-state reference speech models that are specific to the same K groups of one or more other subjects, referred to herein as "reference subjects." In other words, for any speech sample s, the first-state reference speech models return respective first distances $\{D_k^0(s)\}$, k=1 . . . K, which indicate degrees of similarity between s and respective reference first-state speech uttered by the K groups, while the second-state reference speech models return respective second distances $\{D_k^1(s)\}$, k=1 . . . K, which indicate degrees of similarity between s and respective reference second-state speech uttered by the K groups. In some embodiments, each of the reference speech models comprises a parametric statistical speech model, such as a Hidden Markov Model (HMM).

Subsequently, at a speech-sample-receiving step 50, the processor receives one or more first-state speech samples $\{u_m^0\}$ from subject 22 (FIG. 1). Next, at a first first-state-model-generating step 52, the processor computes a function "f" for transforming the set of distances $\{D_k^0(s)\}$ into a single transformed distance $f(\{D_k^0(s)\})$ such that another function of the transformed distances for $\{u_m^0\}$ is minimized with respect to one or more suitable constraints. The processor thus generates $\theta^0$ such that the distance measure returned by $\theta^0$, for any speech sample s, is computed by applying the function "f" to $\{D_k^0(s)\}$.

For example, the processor may identify the function "f" that minimizes the sum $\Sigma_{m=1}^{M}|f(\{D_k^0(u_m)\})|^q$, q≥0, with respect to the constraints. Alternatively, the function "f" may minimize the weighted sum $\Sigma_{m=1}^{M}\beta_m|f(\{D_k^0(u_m)\})|^q$, with respect to the constraints. In such embodiments, the weight $\beta_m$ for each speech sample may be a function of the quality of the sample, in that higher-quality samples may be assigned greater weights. Alternatively or additionally, those speech samples whose transformed distances are greater than a predefined threshold (such as a particular percentile of the transformed distances) may be assumed to be outliers, and may therefore be assigned a weighting of zero.

Subsequently, at a first second-state-model-generating step 54, the processor generates $\theta^1$ by applying the same function to $\{D_k^1(s)\}$. In other words, the processor generates $\theta^1$ such that the distance measure returned by $\theta^1$, for any speech sample s, is equal to $f(\{D_k^1(s)\})$.

Effectively, in technique 46, the processor uses the first-state speech samples of the subject to learn the manner in which the subject's voice in the first state may be best approximated as a function of the voices of the K groups of reference subjects in the first state. The processor then assumes that the same approximation applies to the second state, such that the function used for $\theta^0$ may also be used for $\theta^1$.

As a specific example, the function computed in first-state-model-generating step 52, when applied to $\{D_k^0(s)\}$, may return a weighted average of $\{D'_k^0(s)\}$, $D'_k^0(s)$ being a non-decreasing function of $D_k^0(s)$ such as $|D_k^0(s)|^p$ for p≥1. In other words, the distance measure returned by $\theta^0$, for any speech sample s, may be equal to $\Sigma_{k=1}^{K}w_kD'_k^0(s)$ for K weights $\{w_k\}$, k=1 . . . K. Similarly, in such embodiments, the distance measure returned by $\theta^1$ may be equal to $\Sigma_{k=1}^{K}w_kD'_k^0(s)$, $D'_k^1(s)$ being the same non-decreasing function of $D_k^1(s)$. Effectively, such a function approximates the subject's voice as a weighted average of the voices of the K groups of reference subjects.

In such embodiments, to compute the K weights in first-state-model-generating step 52, the processor may minimize the sum of respective distance measures for $\{u_m^0\}$ with respect to a constraint (e.g., $\Sigma_{k=1}^{K}w_k=1$), the distance measure for each speech sample $u_m$ belonging to $\{u_m^0\}$ being based on the transformed distance $\Sigma_{k=1}^{K}w_kD'_k^0(u_m)$. For example, the processor may minimize, with respect to a validity constraint, $\Sigma_{m=1}^{M}|\Sigma_{k=1}^{K}w_kD'_k^0(u_m)|^q$ for q≥0. (For embodiments in which $D'_k^0(s)=|D_k^0(s)|^p$, q is typically made equal to 1/p.) As noted above, the transformed distances may be weighted, e.g., in response to the varying qualities of the samples.

In some embodiments, to simplify the subject-specific models, the processor nullifies weights that are relatively low, such as weights that are less than a particular percentile of $\{w_k\}$ and/or less than a predefined threshold. The processor may then rescale the remaining non-zero weights such that the sum of the weights is one. For example, the processor may nullify all weights but the largest weight $w_{max}$ such that the distance measure returned by $\theta^0$ is equal to $D'_{k_{max}}^0$, where $k_{max}$ is the index of $w_{max}$. Thus, effectively, the subject's voice may be approximated by that of a single one of the K groups of reference subjects, ignoring the other K−1 groups.

(ii) Second Technique

Figure 3:
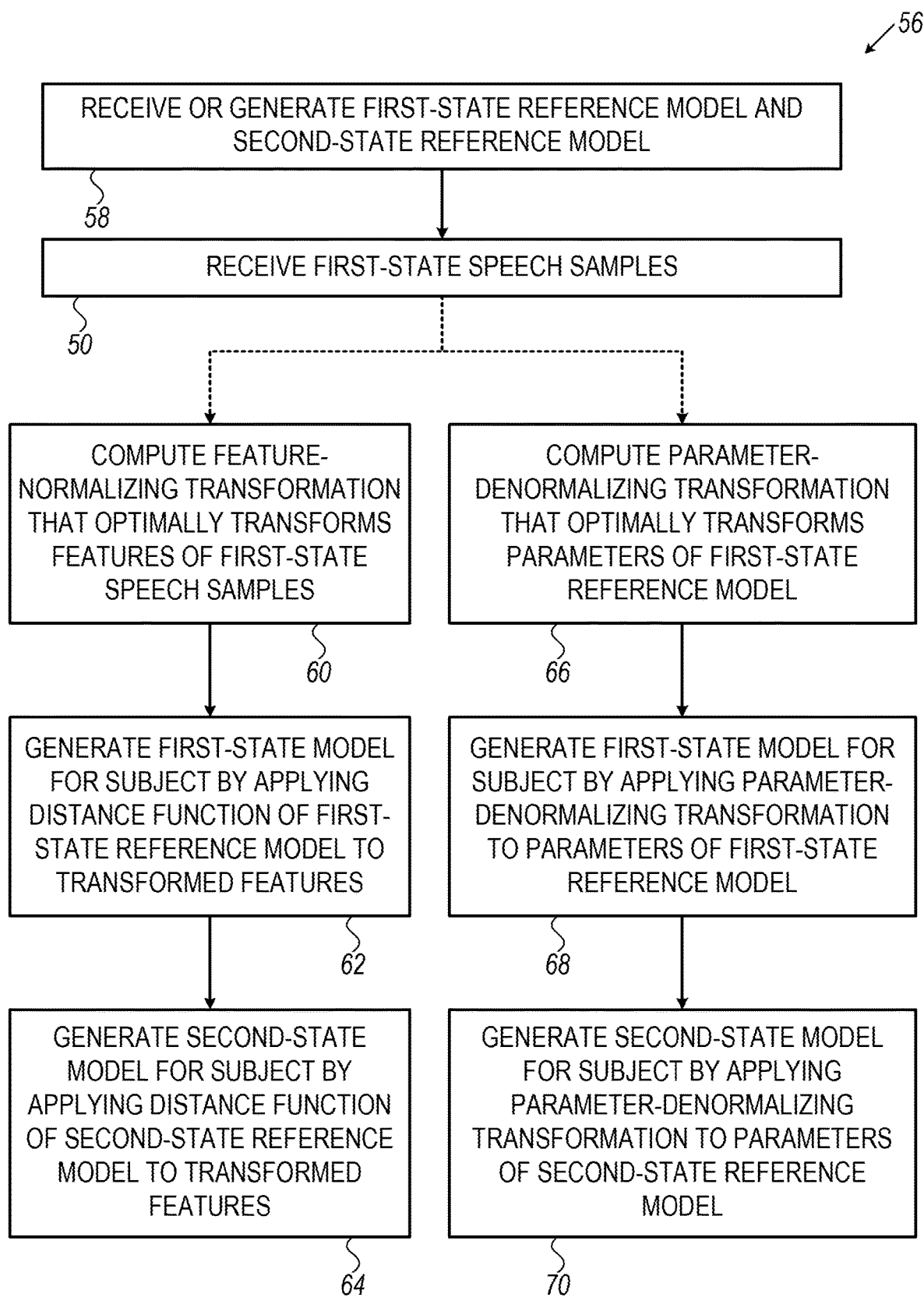

Reference is now made to FIG. 3, which is a flow diagram for a second technique 56 for generating $\theta^0$ and $\theta^1$, in accordance with some embodiments of the present invention.

Technique 56 begins at a second receiving-or-generating step 58, at which the processor receives or generates a first-state reference speech model and a second-state reference speech model (each of which is not specific to the subject). Similarly to each of the first-state reference models in technique 46 (FIG. 2), the first-state reference speech model in technique 56 returns a first distance $D^0(s)$, which indicates a degree of similarity between any speech sample s and reference first-state speech. Likewise, similarly to each of the second-state reference models in technique 46, the second-state reference speech model in technique 56 returns a second distance $D^1(s)$, which indicates a degree of similarity between s and reference second-state speech.

For example, the first-state reference speech model may return $D^0(s)$ by applying a first function $f_0$ to a set $V(s)$ of feature vectors extracted from s (i.e., $D^0(s)$ may equal $f_0(V(s))$), while the second-state reference speech model may return $D^1(s)$ by applying a second function $f_1$ to $V(s)$ (i.e., $D^1(s)$ may equal $f_1(V(s))$). Each of the reference speech models may comprise a parametric statistical speech model, such as a Hidden Markov Model (HMM).

However, as opposed to the case in technique 46, the two reference models are not necessarily generated from reference speech of the same group of subjects. For example, the first-state reference speech model may be generated from reference first-state speech of one group of one or more subjects, while the second-state reference speech model may be generated from reference second-state speech of another group of one or more subjects. Alternatively, one or both of the models may be generated from artificial speech generated by a speech synthesizer. Hence, technique 56 differs from technique 46 as described in detail immediately below.

Subsequently to performing second receiving-or-generating step 58, the processor receives $\{u_m^0\}$ at speech-sample-receiving step 50. Next, in some embodiments, at a transformation-computing step 60, the processor computes a transformation T that optimally transforms $\{V(u_m^0)\}$ under one or more predefined constraints. T may be referred to as a "feature-normalizing" transformation, in that T transforms features of the subject's speech samples so as to neutralize the vocal-tract particularity of the subject, i.e., T renders the speech samples more generic or canonical.

For example, T may minimize $\Sigma_{u \in \{u_m^0\}} f'_0(T(V(u)))$ with respect to a constraint, $f'_0$ being a non-decreasing function of $f_0$. (For example, $f'_0(*)$ may equal $|f_0(*)|^p$ for $p \geq 1$.) Alternatively, T may minimize $\Sigma_{u \in \{u_m^0\}} \Delta(T(V(u)), V(u_0))$ under one or more predefined validity constraints, where $\Delta$ is a distance measure between any two sets of feature vectors, and $u_0$ is, for each sample u belonging to $\{u_m^0\}$, a canonical utterance of the content of u, such as a synthesized utterance of the content. In some embodiments, $\Delta$ is a non-decreasing function of a Dynamic Time Warping (DTW) distance, which may be computed as described in the reference to Sakoe and Chiba cited in the Background, which is incorporated herein by reference. For example, $\Delta(T(V(u)), V(u_0))$ may be equal to $|DTW(T(V(u)), V(u_0))|^p$, where $DTW(V_1, V_2)$ is the DTW distance between two sets of feature vectors $V_1$ and $V_2$, and $p \geq 1$.

(It is noted that, typically, the DTW distance between two sets of feature vectors is computed by mapping each feature vector in one set to a respective feature vector in the other set such that the sum of respective local distances between the pairs of feature vectors is minimized. The local distance between each pair of vectors may be computed by summing the squared differences between the corresponding components of the vectors, or using any other suitable function.)

Typically, the processor extracts, from each received speech sample s, N overlapping or non-overlapping frames, N being a function of the predefined length of each frame. $V(s)$ thus includes N feature vectors $\{v_n\}$, n=1 . . . N, one feature vector per frame. (Each feature vector may include, for example, a set of cepstral coefficients and/or a set of linear prediction coefficients for the frame.) Typically, T includes a transformation that operates on each feature vector independently, i.e., $T(V(s)) = \{T(v_n)\}$, n=1 . . . N. For example, T may include an affine transformation that operates on each feature vector independently, i.e., $T(V(s))$ may be equal to $\{Av_n + b\}$, n=1 . . . N, where A is an L×L matrix and b is an L×1 vector, L being the length of each vector $v_n$.

Subsequently to computing T, the processor, at a second first-state-model-generating step 62, generates $\theta^0$ (the first-state model for the subject) such that, for any speech sample s, $\theta^0$ returns $f_0(T(V(s)))$. Similarly, at a second second-state-model-generating step 64, the processor generates $\theta^1$ such that $\theta^1$ returns $f_1(T(V(s)))$.

In other embodiments, rather than computing T, the processor, at an alternate transformation-computing step 66, computes an alternate transformation T', which optimally transforms parameters of the first-state reference speech model under one or more predefined constraints. For example, the processor may compute T' such that T' minimizes $\Sigma_{u \in \{u_m^0\}} T'(D^0)(u)$ under the constraints, $T'(D^0)(s)$ being the distance returned by the first-state reference speech model under the transformation. Alternatively, subsequently to computing T, the processor may derive T' from T such that applying T' to the model parameters has the same effect as applying T to the features of the subject's speech samples. T' may be referred to as a "parameter-denormalizing" transformation, in that T' transforms the parameters of the reference models to better match the vocal-tract particularity of the subject, i.e., T' renders the reference models more specific to the subject.

In such embodiments, subsequently to computing T', the processor, at a third first-state-model-generating step 68, generates $\theta^0$ by applying T' to parameters of the first-state reference speech model. Similarly, at a third second-state-model-generating step 70, the processor generates $\theta^1$ by applying T' to parameters of the second-state reference speech model. In other words, the processor generates $\theta^0$ such that $\theta^0$ returns, for any speech sample s, $T'(D^0)(s) = f'_0(V(s))$, where $f'_0$ differs from $f_0$ by virtue of using the T'-modified parameters of the first-state reference speech model; similarly, the processor generates $\theta^1$ such that $\theta^1$ returns $T'(D^1)(s) = f'_1(V(s))$, where $f'_1$ differs from $f_1$ by virtue of using the T'-modified parameters of the second-state reference speech model. (For embodiments in which T' is derived from T as described above, $f'_0(V(s)) = f_0(T(V(s)))$ and $f'_1(V(s)) = f_1(T(V(s)))$.)

For example, for cases in which each of the reference speech models includes an HMM including multiple kernels, each subject-specific model may, per the former embodiments, input $T(V(s))$ to the kernels of the corresponding reference speech model. Alternatively, per the latter embodiments, the parameters of the kernels may be transformed using T', and $V(s)$ may then be input to the transformed kernels.

As a specific example, each reference HMM may include multiple Gaussian kernels for each state, each kernel being of the form $$g(v; \mu, \sigma) = \frac{1}{\sqrt{2\pi|\sigma|}} e^{-(v-\mu)^T \sigma^{-1}(v-\mu)},$$

v being any feature vector belonging to $V(s)$, $\mu$ being a mean vector, and $\sigma$ being a covariance matrix having a determinant $|\sigma|$. For example, assuming a state x having J kernels, the local distance between v and x may be computed as $L(\Sigma_{j=1}^{J} w_{x,j} g(v; \mu_{x,j}, \sigma_{x,j}))$, where $g(v; \mu_{x,j}, \sigma_{x,j})$ is the $j^{th}$ Gaussian kernel belonging to state x for j=1 ... J, $w_{x,j}$ is the weight of this kernel, and L is any suitable scalar function such as the identity function or the minus-log function. In this case, T' may include an affine transformation operating on the mean vector of any one or more of the kernels and a quadratic transformation operating on the covariance matrix of any one or more of the kernels. In other words, T' may transform a Gaussian kernel by replacing $\mu$ with $\mu'=A^{-1}(\mu+b)$ and $\sigma$ with $\sigma'=A^{-1}\sigma A^T$, such that, for example, each local distance is computed as $L(\Sigma_{j=1}^J w_{x,j} g(v;\mu'_{x,j},\sigma'_{x,j}))$. (For embodiments in which T' is derived from T as described above, $g(v;\mu'_{x,j},\sigma'_{x,j})$ is equal to $g(T(v);\mu_{x,j},\sigma_{x,j})$, where $T(v)=Av+b$.)

Alternatively, each of the reference speech models may include multiple reference frames. In such embodiments, the distance returned by each reference speech model, for each speech sample s, may be computed (e.g., using DTW) by mapping each feature vector $v_n$ to one of the reference frames such that the sum of the respective local distances between the feature vectors and the reference frames to which the feature vectors are mapped is minimized. In this case, per the former embodiments, each of the subject-specific models may map $\{T(v_n)\}$ to the reference frames of the corresponding reference model for n=1 ... N such that the sum of the local distances is minimized. Alternatively, per the latter embodiments, the features of the reference frames may be transformed using T', and $\{v_n\}$ may then be mapped to the transformed reference frames for n=1 ... N.

Regardless of whether T is applied to the subject's speech samples or T' is applied to the reference models, it is generally advantageous for the reference models to be as canonical or subject-independent as possible. Hence, in some embodiments, particularly if the reference speech used for generating the reference models is from a relatively small number of other subjects, the processor, during receiving-or-generating step 58, normalizes the reference speech prior to generating the reference models.

For example, the processor may first receive first-state reference speech samples uttered by a first subset of R other subjects, along with second-state reference speech samples uttered by a second subset of the other subjects. (The subsets may be overlapping, i.e., at least one of the other subjects may provide both a first-state reference speech sample and a second-state reference speech sample.) Next, for each $r^{th}$ one of the other subjects, the processor may identify $\{\Phi_r\}$, the union of (i) those of the first-state reference speech samples uttered by the $r^{th}$ other subject and (ii) those of the second-state reference speech samples uttered by the $r^{th}$ other subject. Subsequently, the processor may identify respective transformations $\{T_r\}$, r=1 ... R, for the other subjects, $T_r$ being another normalizing transformation that optimally transforms $\{\Phi_r\}$ under the constraints described above. For example, $T_r$ may minimize $\Sigma_{\Phi \in \{\Phi_r\}} \Delta(T(V(\Phi)), V(\Phi_0))$ under predefined validity constraints, $\Phi_0$ being a canonical (e.g., synthesized) utterance of the content of $\Phi$. Next, the processor may compute modified sets of features by, for each $r^{th}$ one of the other subjects, applying $T_r$ to $\{V(\Phi_r)\}$. Finally, the processor may generate the reference discriminator—including both reference models—from the modified sets of features.

(iii) Third Technique

Figure 4:
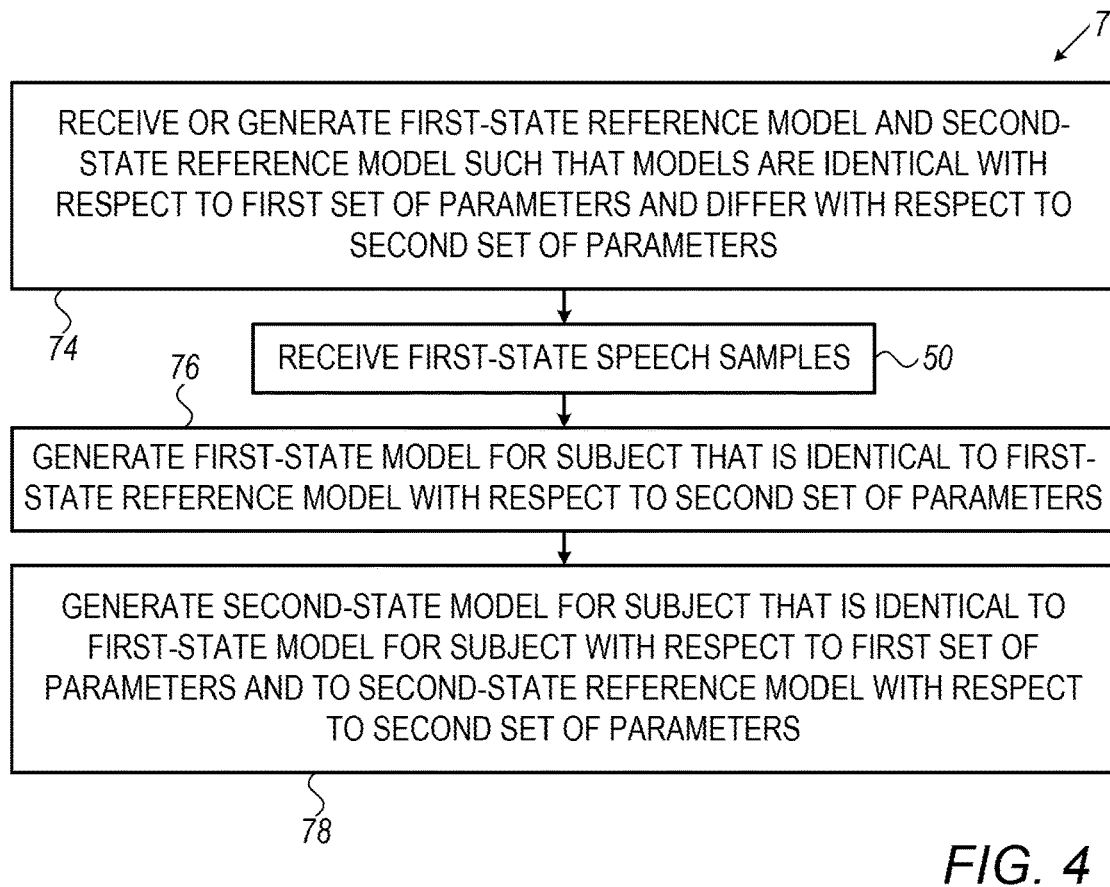

Reference is now made to FIG. 4, which is a flow diagram for a third technique 72 for generating $\theta^0$ and $\theta^1$, in accordance with some embodiments of the present invention.

Similarly to technique 56 (FIG. 3), technique 72 may handle instances in which the first-state reference speech and the second-state reference speech come from different respective groups of subjects. Technique 72 merely requires that the two reference models be identical to one another with respect to a first set of parameters, though differing from one another with respect to a second set of parameters assumed to represent the effect of the subjects' health state on the reference speech. Since this effect is assumed to be the same for subject 22 (FIG. 1), technique 72 generates $\theta^0$ and $\theta^1$ so as to be identical to their corresponding reference models, respectively, with respect to the second set of parameters, while differing with respect to the first set of parameters.

Technique 72 begins at a third receiving-or-generating step 74, at which the processor receives or generates the first-state reference speech model and the second-state reference speech model such that the two models are identical with respect to the first set of parameters and differ from one another with respect to the second set of parameters.

For example, the processor may first receive or generate the first-state reference model. Subsequently, the processor may adapt the second-state reference model to the first-state reference model, by modifying the second set of parameters (without modifying the first set of parameters) such that the sum of the respective distances returned by the second-state reference speech model for the second-state reference speech samples is minimized with respect to a suitable validity constraint. (Any suitable non-decreasing function, such as the absolute value raised to the power of q≥1, may be applied to each of the distances in this summation.) Alternatively, the processor may first receive or generate the second-state reference model, and then adapt the first-state reference model from the second-state reference model.

In some embodiments, the reference models include different respective HMMs, each including multiple kernels having respective kernel weights. In such embodiments, the first set of parameters may include the kernel weights. In other words, the two reference models may include identical states and, in each state, the same number of kernels having the same kernel weights. The first set of parameters may further include the state transition distances or probabilities. The second set of parameters, with respect to which the reference models differ from one another, may include the parameters (e.g., means and covariances) of the kernels.

For example, for the first-state reference model, the local distance between any state x and any feature vector v may be $L(\Sigma_{j=1}^J w_{x,j} g(v;\mu_{x,j}^0,\sigma_{x,j}^0))$. The second-state reference model may include the same states as the first-state reference model, and, for any state x, the local distance may be $L(\Sigma_{j=1}^J w_{x,j} g(v;\mu_{x,j}^1,\sigma_{x,j}^1))$.

Subsequently to third receiving-or-generating step 74, the processor receives $\{u_m^0\}$ at speech-sample-receiving step 50. Next, at a fourth first-state-model-generating step 76, the processor generates $\theta^0$ such that $\theta^0$ is identical to the first-state reference speech model with respect to the second set of parameters. To perform this adaptation of the first-state reference model, the processor may use an algorithm similar to the Baum-Welch algorithm, which is described, for example, in section 6.4.3 of L. Rabiner and B-H. Juang, Fundamentals of Speech Recognition, Prentice Hall, 1993, which is incorporated herein by reference. In particular, the processor may first initialize $\theta^0$ to have the parameters of the first-state reference model. Next, the processor may map each feature vector in $\{u_m^0\}$ to a respective state in $\theta^0$. The processor may then, for each state, use the feature vectors mapped to the state to recompute the first set of parameters for the state. The processor may then remap the feature vectors to the states. This process may then be repeated until convergence, i.e., until the mapping does not change.

Subsequently to fourth first-state-model-generating step 76, the processor, at a fourth second-state-model-generating step 78, generates $\theta^1$ such that $\theta^1$ is identical to $\theta^0$ with respect to the first set of parameters and identical to the second-state reference speech model with respect to the second set of parameters.

Neural-Network Discriminators

In alternate embodiments, the processor synthesizes a subject-specific neural-network discriminator, rather than a multi-model discriminator. In particular, the processor first receives or generates a reference discriminator including a neural network associated with multiple parameters. Subsequently, the processor tunes some of these parameters as described below, thereby adapting the network to subject 22 (FIG. 1).

Figure 5:
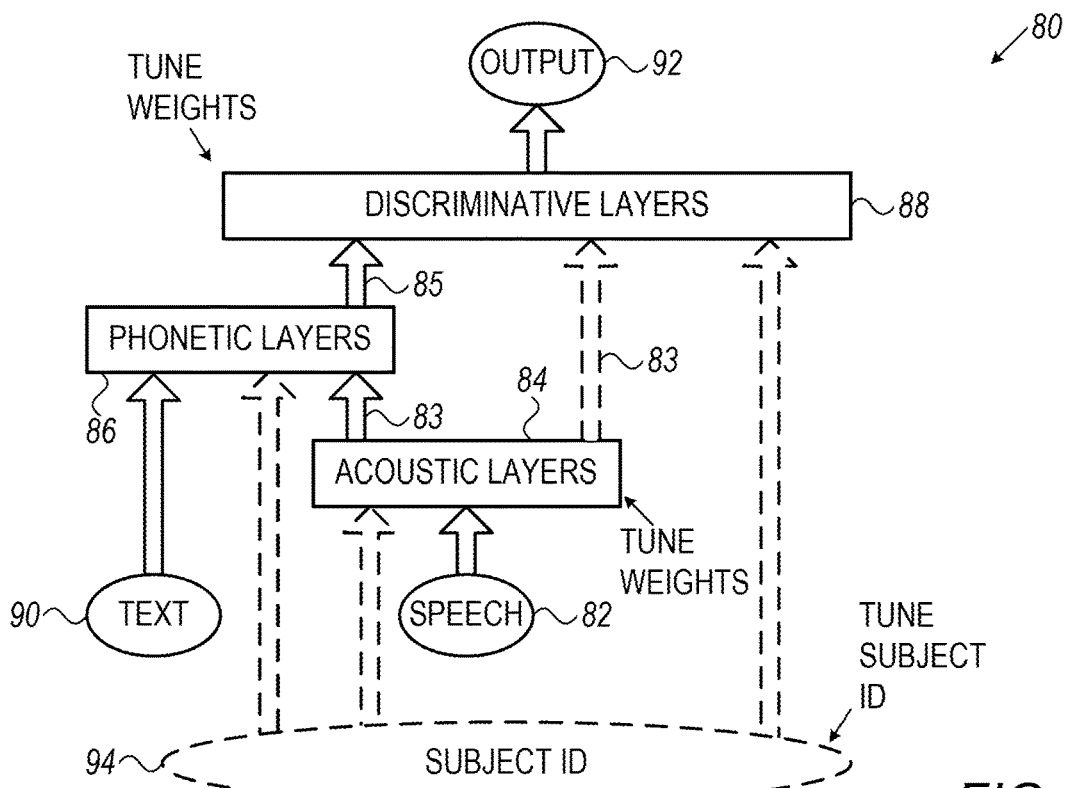
FIG. 5 is a schematic illustration of a neural-network discriminator, in accordance with some embodiments of the present invention.

For further details regarding this technique, reference is now made to FIG. 5, which is a schematic illustration of a neural-network discriminator, in accordance with some embodiments of the present invention.

FIG. 5 shows the manner in which a reference neural network 80 may be adapted to a specific subject. Neural network 80 is configured to receive a speech-related input 82 based on one or more speech samples uttered by a subject. For example, the neural network may receive the speech samples themselves, and/or features, such as mel-frequency cepstral coefficients (MFCCs), extracted from the samples. Neural network 80 may further receive a text input 90 including, for example, an indication of the phonetic content of the speech samples. (The phonetic content may be predetermined, or ascertained from the speech samples using speech-recognition techniques.) For example, if the neural network is trained on N different utterances serially numbered 0 . . . N−1, text input 90 may include a sequence of bits indicating the serial number of the utterance that is uttered in the speech samples.

Given the aforementioned input, the neural network returns an output 92 indicating the likelihood of the speech samples having been uttered in the second state. For example, output 92 may explicitly include the likelihood of the speech samples having been uttered in the second state. Alternatively, the output may explicitly include the likelihood of the speech samples having been uttered in the first state, such that the output implicitly indicates the former likelihood. For example, if the output states a 30% likelihood for the first state, the output may effectively indicate a 70% likelihood for the second state. As yet another alternative, the output may include respective scores for the two states, from which both likelihoods may be calculated.

Typically, neural network 80 includes multiple layers of neurons. For example, for embodiments in which speech-related input 82 includes raw speech samples (rather than features extracted therefrom), the neural network may include one or more acoustic layers 84, which generate an acoustic-layer output 83 in response to speech-related input 82. Effectively, acoustic layers 84 extract feature vectors from the input speech samples by performing an acoustic analysis of the speech samples.

As another example, the neural network may include one or more phonetic layers 86, which generate a phonetic-layer output 85 in response to acoustic-layer output 83 (or in response to analogous features contained in speech-related input 82). For example, phonetic layers 86 may match the acoustic features of the speech samples, which are specified by acoustic-layer output 83, with the expected phonetic content of the speech samples as indicated by text input 90. Alternatively, the network may be configured for a single predefined text, and may thus omit phonetic layers 86 and text input 90.

As yet another example, the neural network may include one or more discriminative layers 88, which generate output 92 in response to phonetic-layer output 85 (and, optionally, acoustic-layer output 83). Discriminative layers 88 may include, for example, one or more layers of neurons that compute features for discriminating between the first health state and the second health state, followed by an output layer, which generates output 92 based on these features. The output layer may include, for example, a first-state output neuron, which outputs a score indicating the likelihood for the first state, and a second-state output neuron, which outputs another score indicating the likelihood for the second state.

In some embodiments, neural network 80 is a deep-learning network, in that the network incorporates a relatively large number of layers. Alternatively or additionally, the network may include specialized elements such as convolutional layers, skipped layers, and/or recurrent neural network components. The neurons in the neural network 80 may be associated with various types of activation functions.

To synthesize a subject-specific neural-network discriminator, the processor tunes a subset of the parameters associated with network 80 so as to minimize an error of output 92 for a set of input speech samples that includes $\{u_m^0\}$. In other words, the processor inputs $\{u_m^0\}$ along with, optionally, one or more speech samples uttered by the subject or by other subjects while in the second state, and tunes the subset of the parameters such that the error of output 92 is minimized.

For example, the processor may tune some or all of the respective neuronal weights of the neurons belonging to the network. As a specific example, the processor may tune at least some of the weights associated with one of the neuronal layers without tuning any of the weights associated with another one of the layers. For example, as indicated in FIG. 5, the processor may tune the weights associated with acoustic layers 84 and/or the weights associated with discriminative layers 88, which are assumed to be subject-dependent, but not the weights associated with phonetic layers 86.

In some embodiments, the neural network is associated with a speaker-identifying (or "subject ID") parameter 94, which identifies the speaker of the speech samples used to generate speech-related input 82. For example, given R serially-numbered reference subjects whose speech was used to train network 80, parameter 94 may include a sequence of R numbers. For each input 82 acquired from one of these subjects, the serial number of the subject may be set to 1 in parameter 94, and the other numbers may be set to 0. Parameter 94 may be input to acoustic layers 84, to phonetic layers 86, and/or to discriminative layers 88.

In such embodiments, the processor may tune parameter 94, alternatively or additionally to tuning the neuronal weights. By tuning parameter 94, the processor may effectively approximate the subject's voice as a combination of the respective voices of some or all of the reference subjects. As a purely illustrative example, for R=10, the processor may tune parameter 94 to a value of [0.5 0 0 0 0.3 0 0 0 0.2 0], indicating that the subject's voice is approximated by a combination of the respective voices of the first, fifth, and ninth reference subjects. (Parameter 94 thus becomes associated with the network by virtue of being a fixed parameter of the network, rather than being associated with the network merely by being a variable input to the network.)

To tune the parameters, the processor may use any suitable technique known in the art. One such technique is back-propagation, which iteratively subtracts, from the parameters, a vector of values that is a multiple of the gradient of a deviation function with respect to the parameters, the deviation function quantifying the deviation between the output and the expected output of the network. Back-propagation may be performed for each sample in the set of input speech samples (optionally with multiple iterations over the samples), until a suitable degree of convergence is reached.

It will be appreciated by persons skilled in the art that the present invention is not limited to what has been particularly shown and described hereinabove. Rather, the scope of embodiments of the present invention includes both combinations and subcombinations of the various features described hereinabove, as well as variations and modifications thereof that are not in the prior art, which would occur to persons skilled in the art upon reading the foregoing description. For example, the scope of embodiments of the present invention includes a synthesis of a single-model subject-specific discriminator, such as a neural-network discriminator, from a reference discriminator including a first-state reference speech model and a second-state reference speech model.

Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

The invention claimed is:

1. Apparatus, comprising:
a communication interface; and
a processor, configured to:
receive, via the communication interface, a plurality of subject-uttered speech samples $\{u_m^0\}$, m=1 ... M, which were uttered by a subject while in a first state with respect to a disease,
obtain at least one reference discriminator that was trained, using multiple reference first-state speech samples uttered in the first state and multiple reference second-state speech samples uttered in a second state with respect to the disease, to discriminate between first-state utterances uttered in the first state and second-state utterances uttered in the second state,
wherein each of the reference first-state speech samples and reference second-state speech samples was not uttered by the subject; and
using $\{u_m^0\}$, even without using any other speech samples uttered by the subject while in the second state, adapt the at least one reference discriminator to the subject.

2. The apparatus according to claim 1, wherein the first state is a stable state and the second state is an unstable state.

3. The apparatus according to claim 1, wherein the disease is selected from the group of diseases consisting of: congestive heart failure (CHF), coronary heart disease, arrhythmia, chronic obstructive pulmonary disease (COPD), asthma, interstitial lung disease, pulmonary edema, pleural effusion, Parkinson's disease, and depression.

4. The apparatus according to claim 1, wherein the processor is configured to adapt the reference discriminator by:

generating a first-state subject-specific speech model $\theta^0$ that returns, for any speech sample s, a first distance measure indicative of a first degree of similarity between s and first-state speech of the subject, and
generating a second-state subject-specific speech model $\theta^1$ that returns a second distance measure indicative of a second degree of similarity between s and second-state speech of the subject.

5. The apparatus according to claim 4,
wherein K first-state subsets of the reference first-state speech samples were uttered, respectively, by K groups of one or more other subjects,
wherein K second-state subsets of the reference second-state speech samples were uttered, respectively, by the K groups,
wherein the at least one reference discriminator includes K reference discriminators $\{\varphi_k\}$, k=1 ... K, $\{\varphi_k\}$ including:
respective first-state reference speech models that return respective first distances $\{D_k^0(s)\}$, which indicate first degrees of similarity between s and the first-state subsets, respectively, and
respective second-state reference speech models that return respective second distances $\{D_k^1(s)\}$, which indicate second degrees of similarity between s and the second-state subsets, respectively,
wherein $\theta^0$ returns the first distance measure by applying a function to $\{D_k^0(s)\}$, and
wherein $\theta^1$ returns the second distance measure by applying the function to $\{D_k^1(s)\}$.

6. The apparatus according to claim 5, wherein the function, when applied to $\{D_k^0(s)\}$, returns a weighted average of $\{D'_k^0(s)\}$, $D'_k^0(s)$ being a non-decreasing function of $D_k^0(s)$.

7. The apparatus according to claim 6, wherein the weighted average is $\Sigma_{k=1}^{K} w_k D'_k^0(s)$ for K weights $\{w_k\}$, k=1 ... K, that minimize a sum of respective distance measures for $\{u_m^0\}$ with respect to a constraint, the distance measure for each speech sample $u_m$ belonging to $\{u_m^0\}$ being based on $\Sigma_{k=1}^{K} w_k D'_k^0(u_m)$.

8. The apparatus according to claim 4, wherein the at least one reference discriminator includes:
a first-state reference speech model that returns a first distance $D^0(s)$, which indicates a first degree of similarity between s and the reference first-state speech samples, and
a second-state reference speech model that returns a second distance $D^1(s)$, which indicates a second degree of similarity between s and the reference second-state speech samples.

9. The apparatus according to claim 8,
wherein the first-state reference speech model returns $D^0(s)$ by applying a first function to a set of feature vectors V(s) extracted from s,
wherein the second-state reference speech model returns $D^1(s)$ by applying a second function to V(s), and
wherein generating $\theta^0$ and $\theta^1$ comprises generating $\theta^0$ and $\theta^1$ using a normalizing transformation T that optimally transforms $\{V(u_m^0)\}$ under one or more predefined constraints.

10. The apparatus according to claim 9, wherein T minimizes $\Sigma_{u \in \{u_m^0\}} \Delta(T(V(u)), V(u_0))$ with respect to a constraint, $\Delta$ being a third distance measure between any two sets of features, and $u_0$ being a canonical utterance of content of $u \in \{u_m^0\}$.

11. The apparatus according to claim 10, wherein Δ is a non-decreasing function of a Dynamic Time Warping (DTW) distance.

12. The apparatus according to claim 9, wherein T minimizes $\Sigma_{u \in \{u_m^0\}} f'_0(T(V(u)))$ with respect to a constraint, $f'_0$ being a non-decreasing function of the first function.

13. The apparatus according to claim 9,
wherein $\theta^0$ returns the first distance measure by applying the first function to T(V(s)), and
wherein $\theta^1$ returns the second distance measure by applying the second function to T(V(s)).

14. The apparatus according to claim 8,
wherein generating $\theta^0$ comprises generating $\theta^0$ by applying a denormalizing transformation T', which optimally transforms first parameters of the first-state reference speech model under one or more predefined constraints, to the first parameters, and
wherein generating $\theta^1$ comprises generating $\theta^1$ by applying T' to second parameters of the second-state reference speech model.

15. The apparatus according to claim 14, wherein T' minimizes $\Sigma_{u \in \{u_m^0\}} T'(D^0)(u)$ under the constraints, $T'(D^0)(s)$ being the first distance returned by the first-state reference speech model under the transformation.

16. The apparatus according to claim 14,
wherein the first-state reference speech model includes a first Hidden Markov Model (HMM) including multiple first kernels, the first parameters including first-kernel parameters of the first kernels, and
wherein the second-state reference speech model includes a second HMM including multiple second kernels, the second parameters including second-kernel parameters of the second kernels.

17. The apparatus according to claim 16, wherein the first kernels and second kernels are Gaussian, and wherein T' includes:
an affine transformation operating on a mean vector of any one or more Gaussian kernels, and
a quadratic transformation operating on a covariance matrix of any one or more Gaussian kernels.

18. The apparatus according to claim 14,
wherein the first-state reference speech model includes multiple first reference frames, the first parameters including first-reference-frame features of the first reference frames, and
wherein the second-state reference speech model includes multiple second reference frames, the second parameters including second-reference-frame features of the second reference frames.

19. The apparatus according to claim 8,
wherein the reference first-state speech samples were uttered by a first subset of R other subjects,
wherein the reference second-state speech samples were uttered by a second subset of the other subjects, and
wherein the processor is configured to obtain the reference discriminator by:
identifying respective transformations $\{T_r\}$, r=1 . . . R, for the other subjects, $T_r$ being, for each $r^{th}$ one of the other subjects, a normalizing transformation that optimally transforms $\{\Phi_r\}$ under one or more predefined constraints, $\{\Phi_r\}$ being a union of (i) those of the reference first-state speech samples uttered by the other subject and (ii) those of the reference second-state speech samples uttered by the other subject,
computing modified sets of features by, for each $r^{th}$ one of the other subjects, applying $T_r$ to $\{V(\Phi_r)\}$, and
generating the reference discriminator from the modified sets of features.

20. The apparatus according to claim 8,
wherein the first-state reference speech model and the second-state reference speech model are identical with respect to a first set of parameters and differ from one another with respect to a second set of parameters,
wherein the processor is configured to generate $\theta^0$ such that $\theta^0$ is identical to the first-state reference speech model with respect to the second set of parameters, and
wherein the processor is configured to generate $\theta^1$ such that $\theta^1$ is identical to $\theta^0$ with respect to the first set of parameters and identical to the second-state reference speech model with respect to the second set of parameters.

21. The apparatus according to claim 20,
wherein the first-state reference speech model and the second-state reference speech model include different respective Hidden Markov Models (HMMs), each including multiple kernels having respective kernel weights,
wherein the first set of parameters includes the kernel weights, and
wherein the second set of parameters includes kernel-parameters of the kernels.

22. The apparatus according to claim 1,
wherein the at least one reference discriminator includes a reference neural network associated with multiple parameters, which returns, for any one or more test speech samples, an output indicating a likelihood of the test speech samples having been uttered in the second state, and
wherein the processor is configured to adapt the reference discriminator by tuning only a subset of the parameters so as to minimize an error of the output for a set of input speech samples that includes $\{u_m^0\}$.

23. The apparatus according to claim 22, wherein the parameters include a plurality of neuronal weights, and wherein the subset of the parameters includes a subset of the weights.

24. The apparatus according to claim 23, wherein the reference neural network includes multiple layers, and wherein the subset of the weights includes at least some of the weights associated with one of the layers but does not include any of the weights associated with another one of the layers.

25. The apparatus according to claim 24,
wherein the layers include (i) one or more acoustic layers of neurons, which generate an acoustic-layer output in response to an input based on the test speech samples, (ii) one or more phonetic layers of neurons, which generate a phonetic-layer output in response to the acoustic-layer output, and (iii) one or more discriminative layers of neurons, which generate the output in response to the phonetic-layer output, and
wherein the subset of the weights includes at least some of the weights associated with the acoustic layers and the discriminative layers but does not include any of the weights associated with the phonetic layers.

26. The apparatus according to claim 22, wherein the subset of the parameters includes a speaker-identifying parameter identifying a speaker of the test speech samples.

27. The apparatus according to claim 22, wherein the set of input speech samples further includes one or more input second-state speech samples.

28. A method, comprising:
receiving a plurality of subject-uttered speech samples $\{u_m^0\}$, m=1 ... M, which were uttered by a subject while in a first state with respect to a disease;
obtaining at least one reference discriminator that was trained, using multiple reference first-state speech samples uttered in the first state and multiple reference second-state speech samples uttered in a second state with respect to the disease, to discriminate between first-state utterances uttered in the first state and second-state utterances uttered in the second state,
wherein each of the reference first-state speech samples and reference second-state speech samples was not uttered by the subject; and
using $\{u_m^0\}$, without using any other speech samples uttered by the subject while in the second state, adapting the at least one reference discriminator to the subject.

29. The method according to claim 28, wherein the first state is a stable state and the second state is an unstable state.

30. The method according to claim 28, wherein the disease is selected from the group of diseases consisting of: congestive heart failure (CHF), coronary heart disease, arrhythmia, chronic obstructive pulmonary disease (COPD), asthma, interstitial lung disease, pulmonary edema, pleural effusion, Parkinson's disease, and depression.

31. The method according to claim 28, wherein adapting the reference discriminator comprises:
generating a first-state subject-specific speech model $\theta^0$ that returns, for any speech sample s, a first distance measure indicative of a first degree of similarity between s and first-state speech of the subject; and
generating a second-state subject-specific speech model $\theta^1$ that returns a second distance measure indicative of a second degree of similarity between s and second-state speech of the subject.

32. The method according to claim 31,
wherein K first-state subsets of the reference first-state speech samples were uttered, respectively, by K groups of one or more other subjects,
wherein K second-state subsets of the reference second-state speech samples were uttered, respectively, by the K groups,
wherein the at least one reference discriminator includes K reference discriminators $\{\varphi_k\}$, k=1 ... K, $\{\varphi_k\}$ including:
respective first-state reference speech models that return respective first distances $\{D_k^0(s)\}$, which indicate first degrees of similarity between s and the first-state subsets, respectively, and
respective second-state reference speech models that return respective second distances $\{D_k^1(s)\}$, which indicate second degrees of similarity between s and the second-state subsets, respectively,
wherein $\theta^0$ returns the first distance measure by applying a function to $\{D_k^0(s)\}$, and
wherein $\theta^1$ returns the second distance measure by applying the function to $\{D_k^1(s)\}$.

33. The method according to claim 32, wherein the function, when applied to $\{D_k^0(s)\}$, returns a weighted average of $\{D'_k^0(s)\}$, $D'_k^0(s)$ being a non-decreasing function of $D_k^0(s)$.

34. The method according to claim 33, wherein the weighted average is $\Sigma_{k=1}^{K} w_k D'_k^0(s)$ for K weights $\{w_k\}$, k=1 ... K, that minimize a sum of respective distance measures for $\{u_m^0\}$ with respect to a constraint, the distance measure for each speech sample $u_m$ belonging to $\{u_m^0\}$ being based on $\Sigma_{k=1}^{K} w_k D'_k^0(u_m)$.

35. The method according to claim 31, wherein the at least one reference discriminator includes:
a first-state reference speech model that returns a first distance $D^0(s)$, which indicates a first degree of similarity between s and the reference first-state speech samples, and
a second-state reference speech model that returns a second distance $D^1(s)$, which indicates a second degree of similarity between s and the reference second-state speech samples.

36. The method according to claim 35,
wherein the first-state reference speech model returns $D^0(s)$ by applying a first function to a set of feature vectors $V(s)$ extracted from s,
wherein the second-state reference speech model returns $D^1(s)$ by applying a second function to $V(s)$, and
wherein generating $\theta^0$ and $\theta^1$ comprises generating $\theta^0$ and $\theta^1$ using a normalizing transformation T that optimally transforms $\{V(u_m^0)\}$ under one or more predefined constraints.

37. The method according to claim 36, wherein T minimizes $\Sigma_{u \in \{u_m^0\}} \Delta(T(V(u)), V(u_0))$ with respect to a constraint, $\Delta$ being a third distance measure between any two sets of features, and $u_0$ being a canonical utterance of content of $u \in \{u_m^0\}$.

38. The method according to claim 37, wherein $\Delta$ is a non-decreasing function of a Dynamic Time Warping (DTW) distance.

39. The method according to claim 36, wherein T minimizes $\Sigma_{u \in \{u_m^0\}} f'_0(T(V(u)))$ with respect to a constraint, $f'_0$ being a non-decreasing function of the first function.

40. The method according to claim 36,
wherein $\theta^0$ returns the first distance measure by applying the first function to $T(V(s))$, and
wherein $\theta^1$ returns the second distance measure by applying the second function to $T(V(s))$.

41. The method according to claim 35,
wherein generating $\theta^0$ comprises generating $\theta^0$ by applying a denormalizing transformation T', which optimally transforms first parameters of the first-state reference speech model under one or more predefined constraints, to the first parameters, and
wherein generating $\theta^1$ comprises generating $\theta^1$ by applying T' to second parameters of the second-state reference speech model.

42. The method according to claim 41, wherein T' minimizes $\Sigma_{u \in \{u_m^0\}} T'(D^0)(u)$ under the constraints, $T'(D^0)(s)$ being the first distance returned by the first-state reference speech model under the transformation.

43. The method according to claim 41,
wherein the first-state reference speech model includes a first Hidden Markov Model (HMM) including multiple first kernels, the first parameters including first-kernel parameters of the first kernels, and
wherein the second-state reference speech model includes a second HMM including multiple second kernels, the second parameters including second-kernel parameters of the second kernels.

44. The method according to claim 43, wherein the first kernels and second kernels are Gaussian, and wherein T' includes:
an affine transformation operating on a mean vector of any one or more Gaussian kernels, and a quadratic transformation operating on a covariance matrix of any one or more Gaussian kernels.

45. The method according to claim 41,
wherein the first-state reference speech model includes multiple first reference frames, the first parameters including first-reference-frame features of the first reference frames, and
wherein the second-state reference speech model includes multiple second reference frames, the second parameters including second-reference-frame features of the second reference frames.

46. The method according to claim 35,
wherein the reference first-state speech samples were uttered by a first subset of R other subjects,
wherein the reference second-state speech samples were uttered by a second subset of the other subjects, and
wherein obtaining the reference discriminator comprises:
identifying respective transformations $\{T_r\}$, r=1 . . . R, for the other subjects, $T_r$ being, for each $r^{th}$ one of the other subjects, a normalizing transformation that optimally transforms $\{\Phi_r\}$ under one or more predefined constraints, $\{\Phi_r\}$ being a union of (i) those of the reference first-state speech samples uttered by the other subject and (ii) those of the reference second-state speech samples uttered by the other subject;
computing modified sets of features by, for each $r^{th}$ one of the other subjects, applying $T_r$ to $\{V(\Phi_r)\}$; and
generating the reference discriminator from the modified sets of features.

47. The method according to claim 35,
wherein the first-state reference speech model and the second-state reference speech model are identical with respect to a first set of parameters and differ from one another with respect to a second set of parameters,
wherein generating $\theta^0$ comprises generating $\theta^0$ such that $\theta^0$ is identical to the first-state reference speech model with respect to the second set of parameters, and
wherein generating $\theta^1$ comprises generating $\theta^1$ such that $\theta^1$ is identical to $\theta^0$ with respect to the first set of parameters and identical to the second-state reference speech model with respect to the second set of parameters.

48. The method according to claim 47,
wherein the first-state reference speech model and the second-state reference speech model include different respective Hidden Markov Models (HMMs), each including multiple kernels having respective kernel weights,
wherein the first set of parameters includes the kernel weights, and
wherein the second set of parameters includes kernel-parameters of the kernels.

49. The method according to claim 28,
wherein the at least one reference discriminator includes a reference neural network associated with multiple parameters, which returns, for any one or more test speech samples, an output indicating a likelihood of the test speech samples having been uttered in the second state, and
wherein adapting the reference discriminator comprises tuning only a subset of the parameters so as to minimize an error of the output for a set of input speech samples that includes $\{u_m^0\}$.

50. The method according to claim 49, wherein the parameters include a plurality of neuronal weights, and wherein the subset of the parameters includes a subset of the weights.

51. The method according to claim 50, wherein the reference neural network includes multiple layers, and wherein the subset of the weights includes at least some of the weights associated with one of the layers but does not include any of the weights associated with another one of the layers.

52. The method according to claim 51,
wherein the layers include (i) one or more acoustic layers of neurons, which generate an acoustic-layer output in response to an input based on the test speech samples, (ii) one or more phonetic layers of neurons, which generate a phonetic-layer output in response to the acoustic-layer output, and (iii) one or more discriminative layers of neurons, which generate the output in response to the phonetic-layer output, and
wherein the subset of the weights includes at least some of the weights associated with the acoustic layers and the discriminative layers but does not include any of the weights associated with the phonetic layers.

53. The method according to claim 49, wherein the subset of the parameters includes a speaker-identifying parameter identifying a speaker of the test speech samples.

54. The method according to claim 49, wherein the set of input speech samples further includes one or more input second-state speech samples.

55. A computer software product comprising a tangible non-transitory computer-readable medium in which program instructions are stored, which instructions, when read by a processor, cause the processor to:
receive a plurality of subject-uttered speech samples $\{u_m^0\}$, m=1 . . . M, which were uttered by a subject while in a first state with respect to a disease,
obtaining at least one reference discriminator that was trained, using multiple reference first-state speech samples uttered in the first state and multiple reference second-state speech samples uttered in a second state with respect to the disease, to discriminate between first-state utterances uttered in the first state and second-state utterances uttered in the second state,
wherein each of the reference first-state speech samples and reference second-state speech samples was not uttered by the subject, and
using $\{u_m^0\}$, even without using any other speech samples uttered by the subject while in the second state, adapting the at least one reference discriminator to the subject.

* * * * *